(12) United States Patent
Stock et al.

(10) Patent No.: US 9,862,708 B2
(45) Date of Patent: Jan. 9, 2018

(54) PYRAZOLONE COMPOUNDS AND USES THEREOF

(71) Applicant: Tempest Therapeutics, Inc., San Francisco, CA (US)

(72) Inventors: Nicholas Simon Stock, Encinitas, CA (US); Austin Chih-Yu Chen, San Marcos, CA (US); Yalda Mostofi Bravo, San Diego, CA (US); Jason Duarte Jacintho, San Diego, CA (US); Yen Truong, San Diego, CA (US)

(73) Assignee: TEMPEST THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 15/118,402

(22) PCT Filed: Feb. 9, 2015

(86) PCT No.: PCT/US2015/015000
§ 371 (c)(1),
(2) Date: Aug. 11, 2016

(87) PCT Pub. No.: WO2015/123133
PCT Pub. Date: Aug. 20, 2015

(65) Prior Publication Data
US 2017/0174666 A1 Jun. 22, 2017

Related U.S. Application Data

(60) Provisional application No. 61/939,955, filed on Feb. 14, 2014.

(51) Int. Cl.
| C07D 231/20 | (2006.01) |
| C07D 231/54 | (2006.01) |
| C07D 401/10 | (2006.01) |
| C07D 401/12 | (2006.01) |
| C07D 405/10 | (2006.01) |

(52) U.S. Cl.
CPC ......... *C07D 405/10* (2013.01); *C07D 231/20* (2013.01); *C07D 231/54* (2013.01); *C07D 401/10* (2013.01); *C07D 401/12* (2013.01)

(58) Field of Classification Search
None
See application file for complete search history.

(56) References Cited

U.S. PATENT DOCUMENTS

| 3,244,593 | A  | 4/1966 | Shoen |
| 4,719,175 | A  | 1/1988 | Chinoporos et al. |
| 5,484,940 | A  | 1/1996 | Grant |
| 5,869,516 | A  | 2/1999 | Arlt |
| 6,455,525 | B1 | 9/2002 | Singh et al. |
| 6,746,989 | B1 | 6/2004 | Mueller |
| 7,060,822 | B1 | 6/2006 | Arnold et al. |
| 2006/0041137 | A1 | 2/2006 | Cao |
| 2009/0069340 | A1 | 3/2009 | Balestra |

FOREIGN PATENT DOCUMENTS

| EP | 0 121 856 | 10/1984 |
| EP | 1 900 728 | 3/2008 |
| EP | 1 905 762 | 4/2008 |

(Continued)

OTHER PUBLICATIONS

Colotta et al., 1993, Novel adenosine receptor ligands: 1,3-disubstituted[1]benzopyrano[2,3-c]pyrazol-4-ones; synthesis and structure-activity relationships, Receptors and Channels, 1(2):111-119.

Grandberg et al., 1968, Pyrazoles. LXV. Synthesis of a series of 5-hydroxy- and 5-aminopyrazoles with nitrogen-containing functional substituents, Khimiko-Farmatsevticheskii Zhurnal, 2(7):24-28.

Guven et al., 1999, A study on the pyrazoles; tautomerism, conformation, acidity, and basicity by means of AM1 semiempirical method in the gas and aqueous solution, Journal of Molecular Structure: Theochem, 488(1-3):125-134.

(Continued)

*Primary Examiner* — Kamal Saeed
(74) *Attorney, Agent, or Firm* — Wilson Sonsini Goodrich & Rosati

(57) ABSTRACT

The invention disclosed herein is directed to compounds of Formula I [Formula should be entered here] and pharmaceutically acceptable salts thereof, which are useful in the treatment of prostate, breast, colon, pancreatic, human chronic lymphocytic leukemia, acute or chronic myeloid leukemia, melanoma, and other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, acute or chronic myeloid leukemia, melanoma and other cancers. The invention disclosed herein is further directed to methods of treating prostate, breast, ovarian, liver, kidney, colon, pancreatic, human chronic lymphocytic leukemia, acute or chronic myeloid leukemia, melanoma and other cancers through the administration of a therapeutically effective amount of a selective PPARα antagonist. The compounds and pharmaceutical compositions of the invention are also useful in the treatment of viral infections, such as HCV infections and HIV infections.

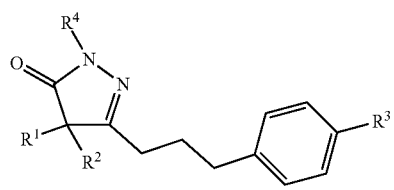

I

19 Claims, No Drawings

(56) References Cited

FOREIGN PATENT DOCUMENTS

| | | |
|---|---|---|
| FR | 2672891 | 2/1994 |
| JP | 02-229168 | 9/1990 |
| WO | WO 96/12706 | 5/1996 |
| WO | WO 01/009121 | 2/2001 |
| WO | WO 08/020150 | 2/2008 |
| WO | WO 09/038411 | 3/2009 |
| WO | WO 10/059241 | 5/2010 |
| WO | WO 12/020738 | 2/2012 |
| WO | WO 12/074067 | 6/2012 |
| WO | WO 12/074068 | 6/2012 |
| WO | WO 13/134562 | 9/2013 |

OTHER PUBLICATIONS

Harran et al., 1975, Association constants study of pyrazolin-5-ones by IR spectroscopy: theoretical approach, Journal de Chimie Physique et de Physico-Chimie Biologique, 72(6):809-811.

Katritzky et al., 1964, Tautomerism of heteroaromatic compounds with five-membered rings. IV. Substituted pyrazolin-5-ones, Tetrahedron, 20(2):299-314.

Katritzky et al., 1965, Tautomerism of heteroaromatic compounds with five-membered rings. IX. N-unsubstituted pyrazolin-3(5)-ones, Tetrahedron, 21(7):1693-1699.

Maquestiau et al., 1973, Mass spectrometry of N1-substituted pyrozolin-5-ones. II. Fixed 2-pyrazolin-5-ones and tautomerizable pyrazolin-5-ones, Bulletin des Societies Chimiques Belges, 82(11-12):757-763.

Ragavan et al., 2009, Synthesis of some novel bioactive 4-oxy/thio substituted-1H-pyrazol-5(4H)-ones via efficient cross-Claisen condensation, European Journal of Medicinal Chemistry, 44:3852-3857.

Shamsuzzaman et al., Jan. 2014, Synthesis, evaluation and docking studies on steroidal pyrazolones as anticancer and antimicobial agents, Med. Chem. Res., 23:348-362.

Wang et al., 2010, A cell-based screen for anticancer activity of 13 pyrazolone derivatives, Chin. J. Cancer, 29:980-987.

Zhang et al., 2000, Nonpeptide endothelin antagonists: from lower affinity pyrazol-5-ols to higher affinity pyrazole-5-carboxylic acids, Bioorganic & Medicinal Chemistry Letters, 10:1351-1355.

International Search Report and Written Opinion dated May 22, 2015 in PCT/US15/015000.

PYRAZOLONE COMPOUNDS AND USES THEREOF

RELATED APPLICATIONS

This application is the National Phase Entry of PCT/2015/015000, filed Feb. 9, 2015, which claims the benefit of U.S. Provisional Patent Application No. 61/939,955, entitled "PYRAZOLONE COMPOUNDS AND USES THEREOF" filed on Feb. 14, 2014, which is incorporated by reference in its entirety.

FIELD OF THE INVENTION

This invention is directed to novel pyrazolones, or pharmaceutically acceptable salts thereof, useful in the treatment of prostate, breast, colon, pancreatic, human chronic lymphocytic leukemia, acute or chronic myeloid leukemia, melanoma and other cancers. The invention disclosed herein is further directed to methods of treating prostate, breast, ovarian, liver, kidney, colon, pancreatic, human chronic lymphocytic leukemia, acute or chronic myeloid leukemia, melanoma and other cancers comprising administration of selective PPARα antagonists. The compounds and pharmaceutical compositions of the invention are also useful in the treatment of viral infections, such as HCV infections and HIV infections.

BACKGROUND OF THE INVENTION

While tremendous strides have been made in the treatment of various cancers, in many cases, cancer treatment continues to be a matter of administering one or more anti-cancer agents that are marginally less chemotoxic to healthy cells than they are to the cancer in question. In recognition of this problem, there has been substantial research effort aimed at identifying, understanding and taking advantage of phenotypical behavior peculiar to certain cancer cells. It has long been observed that most cancer cell types generate energy for cellular processes through aerobic glycolysis rather than through oxidative phosphorylation as found in the normal cell. This process, which became known as the "Warburg effect", is highly energy inefficient and requires cancer cell mitochondria to resort to glucose fermentation to make up the energy deficit. Since perhaps the mid-1990's researchers have sought to identify methods of treating cancer that take advantage of the "Warburg effect" and associated aspects of cancer cell mitochondrial metabolism. See, for example, Wang, et. al., Small mitochondrial-targeting molecules as anti-cancer agents, Mol. Aspects Med. 2010 February; 31(1): 75-92.

Samudio, et. al., J. Clin. Invest. 120: 142-156 (2010), disclosed that in certain leukemia cell lines "mitochondrial uncoupling—the continuing reduction of oxygen without ATP synthesis—has recently been shown in leukemic cells to circumvent the ability of oxygen to inhibit glycolysis, and may promote the metabolic preference for glycolysis by shifting from pyruvate oxidation to fatty acid oxidation (FAO)." Samudio, et. al., also provided data indicating that inhibition of FAO could sensitize human leukemia cells to apoptosis, and further that inhibition of FAO may prove useful in the treatment of leukemia.

PPARα is known to be an important regulator of fatty acid oxidation. See Pyper, et. al., Nucl. Recept. Signal. 8:e002, e002 (2010). It has been reported that expression of the PPARα gene can be higher in human chronic lymphocytic leukemia (CLL) making this cancer type sensitive to therapies aimed at reducing FAO (Samudio et al., J. Clin. Invest. 120:142-156 (2010)). This effect may generalize to several cancer types. For example, ovarian cancer and breast cancer (Linher-Melville et al., 2011, BMC, 4; 11:56), thrive in an adipose rich environment and as a result can be negatively impacted by targeted therapies that reduce fatty acid metabolism (Nieman et al., 2011, Nat Med. 2011 Oct. 30; 17(11):1498-503). Still other cancers that rely on FAO include prostate cancer (Liu, Prostate Cancer Prostatic Dis., 2006; 9(3):230-4), colon cancer (Holla et al., 2011, JCB 286(34):30003-30009), pancreatic cancer (Khasawneh et al., 2009, PNAS, 106(9):3354-3359) and lung cancer (Zaugg et al., 2011, Genes and Development, 25:1041-1051).

GW6471 (Xu, et. al., Nature 415, 813-817 (2002)) and MK-866 (Kehrer, et. al., Biochem. J. 356, 899-906 (2001)) have been identified as antagonists of PPAR. Moreover, MK-866, whose primary activity is as an inhibitor of FLAP, has been disclosed to induce apoptosis in a human chronic lymphocytic leukemia cell line in a FLAP-independent manner; and has also been disclosed to induce apoptosis in prostate and glioblastoma cell lines.

Chronic myeloid leukemia (CML) is a model of hematopoietic stem cell (HSC) disease. In 2008, Ito et al, disclosed evidence linking the loss of promyelocytic leukemia (PML) gene expression with favorable outcomes in CML (Nature, 2008 Jun. 19; 453 (7198) 1072-1078). More recently Ito et al., disclosed that in the PML pathway, loss of PPARδ and accompanying inhibition of mitochondrial FAO induced loss of hematopoietic stem cell (HSC) maintenance (Nature Medicine 18, 1350-1358 (2012)). Moreover, Carracedo et al., disclosed that whereas PML expression allowed luminal filling in 3D basement membrane breast cancer, the effect was reversed by inhibition of FAO (J. Clin. Invest. 2012; 122(9):3088-3100). This and other evidence support our view that inhibition of fatty acid oxidation, via antagonism of PPAR's (including PPARα), will prove effective in inhibiting leukemia stem cell differential, and therefore, prove effective in preventing the onset of and/or recurrence of acute and chronic myeloid leukemia, as well as other cancers.

PPARα antagonists have also been shown to inhibit HCV replication and thereby prove useful in the treatment of HCV infection (Rakic, B. et. al., Chem. & Biol. 13, 23-30 (January 2006)). In some embodiments, PPAR modulators have been shown to inhibit viral transcription and replication and thereby prove useful in the treatment of viral diseases (Capeau et al., PPAR Research Volume 2009, Article ID 393408, 2 pages). In some embodiments, PPARα antagonists are useful in the treatment of HIV infection. PPARα antagonists have also been disclosed to be useful in the treatment of metabolic disorders (WO2012/027482A2). Metabolic disorders include, but are not limited to diabetes, obesity, metabolic syndrome, impaired glucose tolerance, syndrome X, and cardiovascular disease.

SUMMARY OF THE INVENTION

The invention disclosed herein is directed to compounds of Formula I

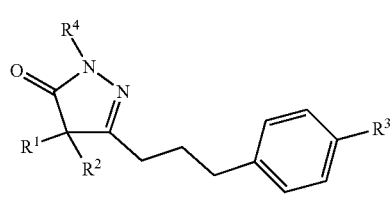

and pharmaceutically acceptable salts thereof, which are useful in the treatment of prostate, breast, colon, pancreatic, human chronic lymphocytic leukemia, acute or chronic myeloid leukemia, melanoma, and other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, acute or chronic myeloid leukemia, melanoma and other cancers. The invention disclosed herein is further directed to methods of treating prostate, breast, ovarian, liver, kidney, colon, pancreatic, human chronic lymphocytic leukemia, acute or chronic myeloid leukemia, melanoma and other cancers through the administration of a therapeutically effective amount of a selective PPARα antagonist. The compounds and pharmaceutical compositions of the invention are also useful in the treatment of viral infections, such as HCV infections and HIV infections.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In one aspect the invention is directed to compounds of Formula I

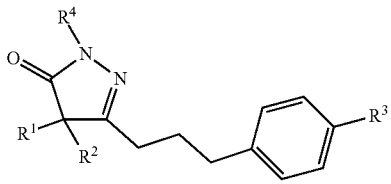

I or a pharmaceutically acceptable salt thereof wherein:
$R^1$ and $R^2$ are each independently —$C_{1-6}$alkyl, optionally mono-, di- or tri-substituted with halogen, or
$R^1$ and $R^2$ are joined together to form —$C_{3-6}$cycloalkyl, optionally mono- or di-substituted with substituents independently selected from halogen, —$C_{1-6}$ alkyl and —$CF_3$;
$R^3$ is selected from the group consisting of:
(a)

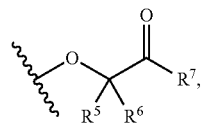

(b) aryl,
(c) heteroaryl,
(d)

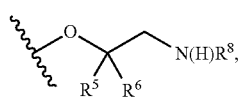

(e)

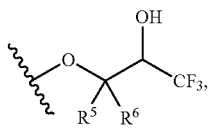

wherein the aryl of choice (b) and the heteroaryl of choice (c) are optionally mono- or di-substituted with substituents independently selected from —N(H)$R^8$, —$C_{1-6}$alkyl, —$C_{1-6}$alkyl-C(=O)OH, —$C_{1-6}$alkoxy, halo-$C_{1-6}$alkyl, halo-$C_{1-6}$alkoxy and,

$R^4$ is selected from the group consisting of:
(a) aryl,
(b) heteroaryl,
(c) —$C_{1-2}$alkyl-aryl, and
(d) —$C_{1-2}$alkyl-heteroaryl,
wherein the aryl of choices (a) and (c), and the heteroaryl of choices (b) and (d), are optionally mono- or di-substituted with substituents selected from the group consisting of halogen, —$C_{1-6}$alkyl, —$CF_3$, —$OCF_3$—$C_{1-6}$alkoxy, —$C_{3-6}$cycloalkoxy, halo-$C_{1-6}$alkyl, aryl, heteroaryl, heterocyclo, —$C_{3-6}$cycloalkyl, and —$C_{3-6}$cycloalkenyl;
$R^5$ and $R^6$ are each independently selected from the group consisting of:
(a) hydrogen,
(b) —$C_{1-6}$alkyl,
(c) aryl, and
(d) hetereoaryl,
wherein the aryl of choice (c) and heteroaryl of choice (d) are optionally mono- or di-substituted with substituents independently selected from halogen, —$C_{1-6}$alkyl and —$CF_3$ or $R^5$ and $R^6$ are joined together to form a —$C_{3-6}$cycloalkyl optionally mono- or di-substituted with substituents independently selected from halogen, —$C_{1-6}$alkyl and —$CF_3$; $R^7$ is selected from the group consisting of:
(a) hydroxyl,
(b) —N(H)S(=O)$_2$aryl,
(c) —N(H)S(=O)$_2$heteroaryl,
(d) —N(H)S(=O)$_2$—$C_{3-6}$cycloalkyl,
(e) —N(H)S(=O)$_2$—$C_{1-6}$alkyl,
(f) —N(H)-aryl,
(g) —N(H)-heteroaryl,
(h) —N(H)—$C_{3-6}$cycloalkyl,
(i) —N(H)—$C_{1-6}$alkyl, and
(j) —$CF_3$,
wherein the aryl of choices (b) and (f), the heteroaryl of choices (c) and (g), the alkyl portion of choices (e) and (i), and the cycloalkyl portion of choices (d) and (h), are optionally mono- or di-substituted with substituents independently selected from halogen, —$C_{1-6}$alkyl, —$CF_3$, —$C_{3-6}$cycloalkyl, —$C_{1-6}$alkoxy, —$C_{3-6}$cycloalkoxy, aryl, heteroaryl, and hydroxyl; and
$R^8$ is selected from the group consisting of:
(a) hydrogen,
(b) —S(=O)$_2$aryl,
(c) —S(=O)$_2$heteroaryl,
(d) —C(=O)aryl,
(e) —C(=O)heteroaryl, (f) —S(=O)$_2$—C$_{1-6}$alkyl,
(g) —S(=O)$_2$—C$_{3-6}$cycloalkyl,
(h) —C(=O)—C$_{1-6}$alkyl, and
(i) —C(=O)—C$_{3-6}$cycloalkyl, wherein the aryl of choices (b) and (d), and the heteroaryl of choices (c) and (e), the alkyl portion of choices (f) and (h), and the cycloalkyl portion of choices (g) and (i), are optionally mono- or di-substituted with substituents independently selected from halogen, —C$_{1-6}$alkyl, —CF$_3$, —C$_{3-6}$cycloalkyl, —C$_{1-6}$alkoxy, —C$_{3-6}$cycloalkoxy, aryl, heteroaryl, and hydroxyl.

Within this aspect there is a genus wherein:
R$^1$ and R$^2$ are each independently methyl, optionally mono-, di- or tri-substituted with halogen or
R$^1$ and R$^2$ are joined together to form —C$_{3-6}$cycloalkyl, optionally mono or di-substituted with substituents independently selected from halogen, —C$_{1-6}$alkyl and —CF$_3$.

Within this genus there is a sub-genus wherein:
R$^1$ and R$^2$ are each independently methyl, optionally mono-, di- or tri-substituted with halogen.

Within this aspect there is a genus of Formula Ia

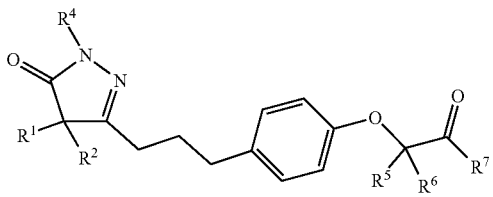

or a pharmaceutically acceptable salt thereof.

Within this aspect there is a genus wherein:
R$^4$ is selected from the group consisting of:
(a) -phenyl,
(b) -pyridyl,
(c) —CH$_2$-phenyl, and
(d) —CH$_2$-pyridyl, wherein the phenyl portion of choices (a) and (c), and the pyridyl portion of choices (b) and (d), are optionally mono- or di-substituted with substituents selected from the group consisting of halogen, —C$_{1-6}$alkyl, —CF$_3$, —OCF$_3$, —C$_{1-6}$alkoxy, —C$_{3-6}$cycloalkyl, —C$_{3-6}$cycloalkoxy, and halo-C$_{1-6}$alkyl.

Within this aspect there is a genus wherein:
R$^5$ and R$^6$ are joined together to form a —C$_{3-6}$cycloalkyl.

Within this aspect there is a genus wherein:
R$^7$ is selected from the group consisting of:
(a) hydroxyl,
(b) —N(H)S(=O)aryl,
(c) —N(H)S(=O)$_2$heteroaryl,
(d) —N(H)S(=O)$_2$—C$_{3-6}$cycloalkyl, and
(e) —N(H)S(=O)$_2$—C$_{1-6}$alkyl, wherein the aryl portion of choice (b), the heteroaryl portion of choice (c), the cycloalkyl portion of choice (d) and the alkyl portion of choice (e) are optionally mono- or di-substituted with substituents independently selected from halogen, —C$_{1-6}$alkyl, —CF$_3$, —C$_{3-6}$cycloalkyl, —C$_{1-6}$alkoxy, —C$_{3-6}$cycloalkoxy, aryl, heteroaryl, and hydroxyl.

Within this genus there is a sub-genus wherein:
R$^7$ is hydroxyl.

Within this aspect there is a genus wherein:
R$^8$ is selected from the group consisting of:
(a) hydrogen,
(b) —S(=O)$_2$aryl,
(c) —S(=O)$_2$heteroaryl,
(d) —C(=O)aryl, and
(e) —C(=O)heteroaryl, wherein the aryl of choices (b) and (d), and the heteroaryl of choices (c) and (e), are optionally mono- or di-substituted with substituents independently selected from halogen, —C$_{1-6}$alkyl, —CF$_3$, —C$_{3-6}$cycloalkyl, —C$_{1-6}$alkoxy, —C$_{3-6}$cycloalkoxy, aryl, heteroaryl, and hydroxyl.

Within this aspect there is a genus of Formula Ia

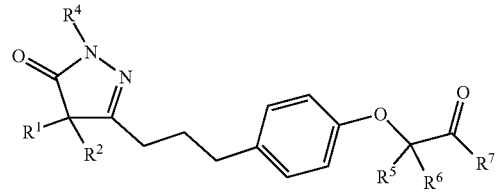

or a pharmaceutically acceptable salt thereof wherein:
R$^1$ and R$^2$ are each independently methyl, optionally mono-, di- or tri-substituted with halogen or
R$^1$ and R$^2$ are joined together to form —C$_{3-6}$cycloalkyl, optionally mono or di-substituted with substituents independently selected from halogen, —C$_{1-6}$alkyl and —CF$_3$;
R$^4$ is selected from the group consisting of:
(a) -phenyl,
(b) -pyridyl,
(c) —CH$_2$-phenyl, and
(d) —CH$_2$-pyridyl, wherein the phenyl portion of choices (a) and (c), and the pyridyl portion of choices (b) and (d), are optionally mono- or di-substituted with substituents selected from the group consisting of halogen, —C$_{1-6}$alkyl, —CF$_3$, —OCF$_3$, —C$_{1-6}$alkoxy, —C$_{3-6}$cycloalkyl, —C$_{3-6}$cycloalkoxy, and halo-C$_{1-6}$alkyl;
R$^5$ and R$^6$ are joined together to form a —C$_{3-6}$cycloalkyl; and
R$^7$ is selected from the group consisting of:
(a) hydroxyl,
(b) —N(H)S(=O)$_2$aryl,
(c) —N(H)S(=O)$_2$heteroaryl,
(d) —N(H)S(=O)$_2$—C$_{3-6}$cycloalkyl, and
(e) —N(H)S(=O)$_2$—C$_{1-6}$alkyl, wherein the aryl portion of choice (b), the heteroaryl portion of choice (c), the cycloalkyl portion of choice (d) and the alkyl portion of choice (e) are optionally mono- or di-substituted with substituents independently selected from halogen, —C$_{1-6}$alkyl, —CF$_3$, —C$_{3-6}$cycloalkyl, —C$_{1-6}$alkoxy, —C$_{3-6}$cycloalkoxy, aryl, heteroaryl, and hydroxyl.

Within this genus there is a sub-genus wherein:
R$^7$ is hydroxyl.

In another aspect the invention is directed to a pharmaceutical composition comprising a compound of Formula I (and/or a compound of any of the other formulae described herein), or a pharmaceutically acceptable salt thereof, and a pharmaceutically acceptable carrier.

In another aspect the invention is directed to a method of treating a cancer which is negatively impacted by diminution in its metabolism of fatty acid oxidation via the administration of a therapeutically effective amount of a compound of Formula I, or a pharmaceutically acceptable salt thereof.

Within this aspect there is a genus wherein the cancer is selected from prostate, breast, ovarian, liver, kidney, colon, pancreatic, human chronic lymphocytic leukemia, acute or chronic myeloid leukemia, and melanoma.

In another aspect the invention is directed to a method of treating cancer comprising the administration of a therapeutically effective amount of a compound of Formula I, or a pharmaceutically acceptable salt thereof.

In another aspect the invention is directed to a method of preventing the onset of and/or recurrence of acute and chronic myeloid leukemia, as well as other cancers, through the administration of a therapeutically effective amount of a compound of Formula I, or a pharmaceutically acceptable salt thereof.

Definitions

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. In some embodiments, an alkyl is a $C_{1-6}$alkyl. Any atom can be optionally substituted, e.g., by one or more substituents. Examples of alkyl groups include without limitation methyl, ethyl, n-propyl, isopropyl, n-butyl, sec-butyl and tert-butyl.

The term "haloalkyl" refers to an alkyl group, in which at least one hydrogen atom is replaced by halo.

In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents. In some embodiments, a haloalkyl is a $C_{1-6}$haloalkyl. In some embodiments, a fluoroalkyl is a $C_{1-6}$fluoroalkyl.

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thioalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. In some embodiments, an alkenyl is a $C_{2-6}$alkenyl.

The term "heterocycle" or "heterocyclic" includes heterocycloalkyls and heteroaryls.

The term "heterocycloalkyl" as used herein except where noted, represents a stable 3-, 4-, 5-, 6- or 7-membered monocyclic- or stable 6-, 7-, 8-, 9-, 10-, 11-, or 12-membered fused bicyclic heterocyclic ring system which comprises at least one non-aromatic (i.e. saturated or partially unsaturated) ring which consists of carbon atoms and from one to four heteroatoms selected from the group consisting of N, O and S, wherein the nitrogen and sulfur heteroatoms may optionally be oxidized, and wherein the nitrogen heteroatom may optionally be quaternized. In some embodiments, a heterocycloalkyl is a $C_{2-10}$heterocycloalkyl. In other embodiments, a heterocycloalkyl is a $C_{2-6}$heterocycloalkyl. In some embodiments, a heterocycloalkyl is monocyclic. In some embodiments, a heterocycloalkyl is bicyclic. In the case of a "heterocycloalkyl" which is a bicyclic group, the second ring may also be a non-aromatic ring which consists of carbon atoms and from one to four heteroatoms selected from the group consisting of N, O and S, as defined above, or the second ring may be a benzene ring, or a "cycloalkyl", or a "cycloalkenyl", as defined immediately below. Examples of such heterocyclic groups include, but are not limited to, aziridine, azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, pyran, pyrazolidine, pyrazoline, pyrrolidine, pyrroline, tetrahydrofuran, tetrahydropyran, thiamorpholine, thiazoline, thiazolidine, thiomorpholine, and N-oxides thereof.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl). In some embodiments, a cycloalkyl is a $C_{3-10}$cycloalkyl. In other embodiments, a cycloalkyl is a $C_{3-6}$cycloalkyl. In some embodiments, a cycloalkyl is monocyclic. In some embodiments, a cycloalkyl is bicyclic.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclopentenyl, cyclohexenyl, cyclohexadienyl, or norbornenyl. In some embodiments, a cycloalkenyl is a $C_{4-10}$cycloalkenyl. In other embodiments, a cycloalkenyl is a $C_{4-6}$cycloalkenyl. In some embodiments, a cycloalkenyl is monocyclic. In some embodiments, a cycloalkenyl is bicyclic.

The term "cycloalkylene", as used herein, refers to a divalent monocyclic cycloalkyl group having the indicated number of ring atoms.

The term "heterocycloalkylene", as used herein, refers to a divalent monocyclic heterocyclyl group having the indicated number of ring atoms.

The term "aryl" as used herein, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, or biphenyl.

The term "heteroaryl", as used herein except where noted, represents a stable 5-, 6- or 7-membered monocyclic- or stable 9 or 10-membered fused bicyclic ring system which comprises at least one aromatic ring, —which consists of carbon atoms and from one to four heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, "heteroaryl" includes, for example, a stable 5-, 6- or 7-membered monocyclic aromatic ring consisting of carbon atoms and from one to four heteroatoms, as defined immediately above, fused to a benzene ring, or fused to a "heterocycloalkyl", a "cycloalkyl", or a "cycloalkenyl", as defined above. Examples of such heteroaryl groups include, but are not limited to, benzimidazole, benzisothiazole, benzisoxazole, benzofuran, isobenzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

Compound Forms and Salts

The compounds of this invention may contain one or more asymmetric centers and thus occur as racemates and racemic mixtures, enantiomerically enriched mixtures, single enantiomers, individual diastereomers and diastereomeric mixtures. The compounds of this invention include all cis, trans, syn, anti, entgegen (E), and zusammen (Z) isomers as well as the appropriate mixtures thereof. The compounds of this invention may also be represented in multiple tautomeric forms, in such instances, the invention expressly includes all tautomeric forms of the compounds described herein, even though only a single tautomeric form may be represented. All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids.

When the compound of the present invention is acidic, salts may be prepared from pharmaceutically acceptable non-toxic bases, including inorganic and organic acids. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8] each of which is incorporated herein by reference in their entireties.

The compounds may be radiolabeled with radioactive isotopes, such as for example tritium, iodine-125 or carbon-14. All isotopic variations of the compounds of the invention, whether radioactive or not, are intended to be encompassed within the scope of the invention.

In some embodiments, hydrogen atoms of the compounds described herein may be replaced with deuterium atoms.

In some embodiments, compounds of Formula I are prepared as prodrugs. Prodrugs are generally drug precursors that, following administration to a subject and subsequent absorption, are converted to an active, or a more active species via some process, such as conversion by a metabolic pathway. Examples of prodrugs include $C_{1-6}$ alkyl esters of carboxylic acid groups, which, upon administration to a subject, are capable of providing active compounds.

Pharmaceutical Compositions

The term "pharmaceutically acceptable carrier" refers to a carrier or an adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Uses

In one aspect the invention disclosed herein is directed to compounds of Formula I and pharmaceutically acceptable salts thereof, which are useful in the treatment of prostate, breast, ovarian, liver, kidney, colon, pancreatic, human chronic lymphocytic leukemia, acute or chronic myeloid leukemia, melanoma and other cancers. In another aspect, the invention is directed to a method of preventing the onset of and/or recurrence of acute and chronic myeloid leukemia, as well as other cancers. The invention also includes pharmaceutical compositions comprising a therapeutically effective amount of compound of Formula I, or a pharmaceutically acceptable salt thereof. The invention disclosed herein is also directed to methods of treating prostate, breast, ovarian, liver, kidney, colon, pancreatic, human chronic lymphocytic leukemia, acute or chronic myeloid leukemia, melanoma and other cancers. The invention disclosed herein is further directed to methods of treating prostate, breast, colon, pancreatic, human chronic lymphocytic leukemia, acute or chronic myeloid leukemia, melanoma and other cancers comprising administration of a therapeutically effective amount of a selective PPARα antagonist. The methods include administering to the subject an effective amount of a compound of Formula (I) (and/or a compound of any of the other formulae described herein) or a salt (e.g., a pharmaceutically acceptable salt) thereof as defined anywhere herein to the patient. In another aspect, the use of a compound of Formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, alleviating, or slowing the progression of) or prevention (e.g., delaying the onset of or reducing the risk of developing) of one or more diseases, disorders, or conditions caused by, or associated with, prostate, breast, ovarian, liver, kidney, colon, pancreatic, human chronic lymphocytic leukemia, acute or chronic myeloid leukemia, melanoma and other cancers.

In one aspect the invention is directed a method of treating a cancer which is negatively impacted by diminution in its metabolism via fatty acid oxidation, comprising administration of a therapeutically effective amount of a compound of Formula I (and/or a compound of any of the other formulae described herein) or a salt (e.g., a pharmaceutically acceptable salt) there of. In another aspect, the invention is directed to a method of treating a cancer having a metabolism that is reliant on fatty acid oxidation, comprising administration of a therapeutically effective amount of a compound of Formula I (and/or a compound of any of the other formulae described herein), or a pharmaceutically acceptable salt thereof.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In one aspect the compounds of the invention may be co-administered with one or more additional anti-cancer agents. The additional anti-cancer agents include, but are not limited to alkylating agents such as cyclophosphamide, chlorambucil, mecloreethamine, ifosfamide, or melphalan; antimetabolites such as methotrexate, cytarabine, fludarabine, 6-mercaptopurine, azathioprene, pyrimidines, or 5-fluorouracil; antimitotic agents such as vincristine, paclitaxel, vinorelbine or docetaxaxel; a topoisomerase inhibitors such as doxorubicin or irinotecan; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib, gefitinib or erlotinib; monoclonal antibodies such as rituximab, trastuzumab, gemtuzumab or ozogamicin; differentiating agents such as tretinoin or arsenic trioxide; antiangiogenic agents such as bevacizumab, sorafinib or sunitinib; biologic response modifiers such as interferon-alpha; topoisomerase inhibitors such as camptothecins (including irinotecan and topotecan), amsacrine, etoposide, etoposide phosphate, or teniposide; cytotoxic antibiotics such as actinomycin, anthracyclines including doxorubicin, daunorubicin, valrubicin, idarubicin, epirubicin, bleomycin, plicamycin or mitomycin; vinca alkaloids such as vincristine, vinblastine, viorelbine or vindesine; podophyllotoxins such as etoposide and teniposide; or mTOR inhibitors such as rapamycin, temsirolimus and everolimus.

Other anti-cancer agents for use in combination with the compounds include one or more of the following: abiraterone; adriamycin; acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; everolimus; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rapamycin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; temsirolimus; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In certain embodiments, the additional agents may be administered separately (e.g., sequentially; on different overlapping schedules), as part of a multiple dose regimen, from the compounds of this invention (e.g., one or more compounds of Formula (I) and/or a compound of any of the other formulae, including any subgenera or specific compounds thereof). In other embodiments, these agents may be part of a single dosage form, mixed together with the compounds of this invention in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the invention can be demonstrated by one or more of the following methods or other methods known in the art:

Human PPARα Reporter Assay

The screening of test compounds for agonist or antagonist activities against human PPARα receptors was performed using a commercial kit, Human PPARα Reporter Assay System (Indigo Biosciences, Cat. #IB00111).

This nuclear receptor assay system utilizes proprietary non-human mammalian cells engineered to provide constitutive, high-level expression of Human PPARα. Because these cells incorporate a PPARα-responsive luciferase reporter gene, quantifying expressed luciferase activity provides a sensitive surrogate measure of PPARα activity in the treated cells. The primary application of this reporter assay system is in the screening of test samples to quantify any functional activity, either agonist or antagonist, that they may exert against human PPARα.

While this assay may be used to measure agonism, each of the Examples, vide infra, exhibits antagonism rather than agonism. Briefly, reporter cells are dispensed into wells of the assay plate and then immediately dosed with test compounds. Following an overnight incubation, the treatment media is discarded and Luciferase Detection Reagent (LDR) is added. The intensity of light emission from the ensuing luciferase reaction provides a sensitive measure that is directly proportional to the relative level of PPARα activation in the reporter cells.

| Example | PPARα $IC_{50}$ (nM) | MS* (ESI) |
|---|---|---|
| 1 | 15 | 479 |
| 2 | 2.1 | 618 |
| 3 | 160 | 568 |
| 4 | 240 | 569 |
| 5 | 280 | 569 |
| 6 | 420 | 574 |
| 7 | 900 | 491 |
| 8 | 62 | 491 |
| 9 | 1,000 | 437 |
| 10 | 410 | 409 |
| 11 | 8.1 | 465 |
| 12 | 22 | 465 |
| 13 | 360 | 501, 503 |
| 14 | 260 | 499 |
| 15 | 130 | 503 |
| 16 | 140 | 463 |
| 17 | 140 | 505 |
| 18 | 120 | 509 |
| 19 | 3.8 | 477 |
| 20 | 19 | 477 |
| 21 | 35 | 478 |
| 22 | 0.90 | 616 |
| 23 | 13 | 505 |
| 24 | 1.4 | 503 |
| 25 | 1.0 | 642 |
| 26 | 110 | 542 |
| 27 | 410 | 584 |
| 28 | 0.97 | 519 |
| 29 | 69 | 558 |
| 30 | 710 | 600 |
| 31 | 2.6 | 463 |
| 32 | 250 | 502 |
| 33 | 500 | 544 |
| 34 | 960 | 517 |
| 35 | 32 | 503 |
| 36 | 27 | 519 |
| 37 | 2.8 | 485 |
| 38 | 25 | 511 |
| 39 | 3.1 | 517 |
| 40 | 20 | 491 |
| 41 | 15,000 | 533 |
| 42 | 34,000 | 533 |
| 43 | 1,200 | 531 |
| 44 | 610 | 529 |
| 45 | 840 | 488 |
| 46 | 1,300 | 628 |
| 47 | 580 | 592 |
| 48 | 4.7 | 525 |
| 49 | 54 | 449 |
| 50 | 2.4 | 489 |
| 51 | 58 | 489 |
| 52 | 4.1 | 503 |
| 53-enantiomer#1 | 820 | 539 |
| 53-enantiomer#2 | 2.1 | 539 |
| 54-enantiomer#1 | 640 | 539 |
| 54-enantiomer#2 | 8.9 | 539 |
| 55 | 110 | 555 |
| 57 | 54 | 553 |
| 58 | 880 | 525 |
| 59 | 430 | 609 |
| 60 | 10 | 639 |

*mass spectroscopic data

Target Selectivity Assays

To determine species selectivity, a Mouse PPARα Reporter Assay System was used (Indigo Biosciences, Cat. #M00111). Activity of test compounds to antagonize or agonize other isoforms of human PPAR, for example β/δ and γ, were assessed using the corresponding kits from Indigo Biosciences (Cat. #IB00121 and #IB00101, respectively). In addition to PPAR activity, compounds were also screened for activity against other nuclear hormone receptors including Estrogen Receptor β, Glucocorticoid Receptor and Thyroid Receptor β using commercially available kits (Indigo Biosciences, Cat. #IB00411, IB00201 and IB01101, respectively). Each assay system from Indigo Biosciences uses technology analogous to the human PPARα kit, with the variance being that the cells used for each assay were engineered to over-express the receptor of interest. In addition, the appropriate receptor agonist (included with each kit) was used at ~$EC_{80}$ for assays in which antagonist potency was being assessed.

Target Selectivity—Counterscreen Assay Results

| Example | PPAR alpha $IC_{50}$ (nM) | PPAR beta/delta $IC_{50}$ (nM) | PPAR gamma $IC_{50}$ (nM) | Thyroid Receptor β $IC_{50}$ (nM) | Glucocorticoid Receptor $IC_{50}$(nM) | Estrogen Receptor β $IC_{50}$(nM) |
|---|---|---|---|---|---|---|
| 50 | 2.4 | 22,000 | 56,000 | 61,000 | 36,000 | 36,000 |

Measurement of Cell Viability

Purified CLL cells were cultured at $2 \times 10^5$ cells/200 μL of RPMI1640 supplemented with 10% FCS in 96-well plates under various treatment conditions. Determination of CLL cell viability was based on the analysis of mitochondrial transmembrane potential ($\Delta\Psi m$) using 3,3'-dihexyloxacarbocyanine iodide (DiOC6) (Invitrogen) and cell membrane permeability to propidium iodide (PI) (Sigma). For viability assays, 100 μL of the cell culture was collected at the indicated time points and transferred to polypropylene tubes containing 100 μL of 40 μM DiOC6 and 10 μg/mL PI in culture media. The cells were then incubated at 37° C. for 15 min and analyzed within 30 min by flow cytometry using an Accuri C6 flow cytometer. The percentage of viable cells was determined by gating on PI negative and DiOC6 bright cells.

In Vivo Cancer Model: B16F10 Model of pulmonary Metastasis

B16F10 cells are cultured in standard growth media, harvested when approximately 50% confluent and injected into C57BL/6 mice via the tail vein (50,000 cells per mouse in 200 μL). Mice are then treated daily with test compound. On day 21, mice are euthanized. Lungs are harvested and placed into Fekete's solution overnight to facilitate visualization of the tumors. Black nodules are enumerated.

Statistics are performed by ANOVA with Dunnett's Multiple Comparison Test post-hoc to determine statistical differences from vehicle treatment group (* denotes P<0.05 while *** denotes P<0.001).

Synthesis

The starting materials used for the synthesis are either synthesized or obtained from commercial sources, such as, but not limited to, Sigma-Aldrich, Fluka, Acros Organics, Alfa Aesar, VWR Scientific, and the like. General methods for the preparation of compounds can be modified by the use of appropriate reagents and conditions for the introduction of the various moieties found in the structures as provided herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

General Synthetic Scheme for Exemplary Compounds

The pyrazalone core found in the exemplified compounds could be conveniently accessed, for example, from the corresponding carboxylic acid (I, Scheme 1) via its initial decarboxylative Claisen condensation with an appropriate monoester of malonic acid (II, Scheme 1). This condensation can, for example, be carried out in the presence of an appropriate activating reagent such as carbonyldiimidazole (i.e. CDI), an appropriate Lewis acid such as magnesium chloride, and an appropriate base such as triethylamine (i.e. TEA). The resulting β-ketoester III could then be di-alkylated, either sequentially or in one-pot, by, for example, its treatment with an appropriate base such as NaH, $Cs_2CO_3$, $K_2CO_3$, or others, followed by the addition of a suitable alkylating reagent, denoted generically as $R^1$—X and $R^2$—X in scheme 1. In examples where $R^1$ and $R^2$ are joined to form a ring, the requisite intermediate could most conveniently be synthesized using, for example, ring closing metathesis whereby the olefin functional group present in both $R^1$ and $R^2$ in IV are welded together by a suitable mediator, such as Grubb's (both generation 1 and generation 2) or Schrock's metathesis catalyst, with the concomitant extrusion of ethene gas. Subsequent hydrogenation of the resulting cyclic alkene, using for example hydrogen gas and palladium, would deliver the requisite saturated carbacyle V. Heating either IV or V with hydrazine in an alcohol solvent such as, for example, ethanol or methanol, in an enclosed reaction vessel would then furnish pyrazolone VI. This could in turn be functionalized, as appropriate, via either a simple nucleophilic displacement reaction (in instances where $R^4$ is an alkyl or heteroalkyl group) or via copper catalyzed N-arylation reaction (in instances where $R^4$ is an aryl or heteroaryl group). In the former case, a base such as, though not limited to, NaH, $Cs_2CO_3$ or $K_2CO_3$ is added along with $R^4$—X to pyrazalone VI in a polar, aprotic solvent. In the latter case, a convenient source of copper(I) such as copper iodide, a suitable ligand such as proline, and a suitable base such as $Cs_2CO_3$, are heated along with to $R^4$—X to pyrazalone VI in a polar, aprotic solvent.

Scheme 1

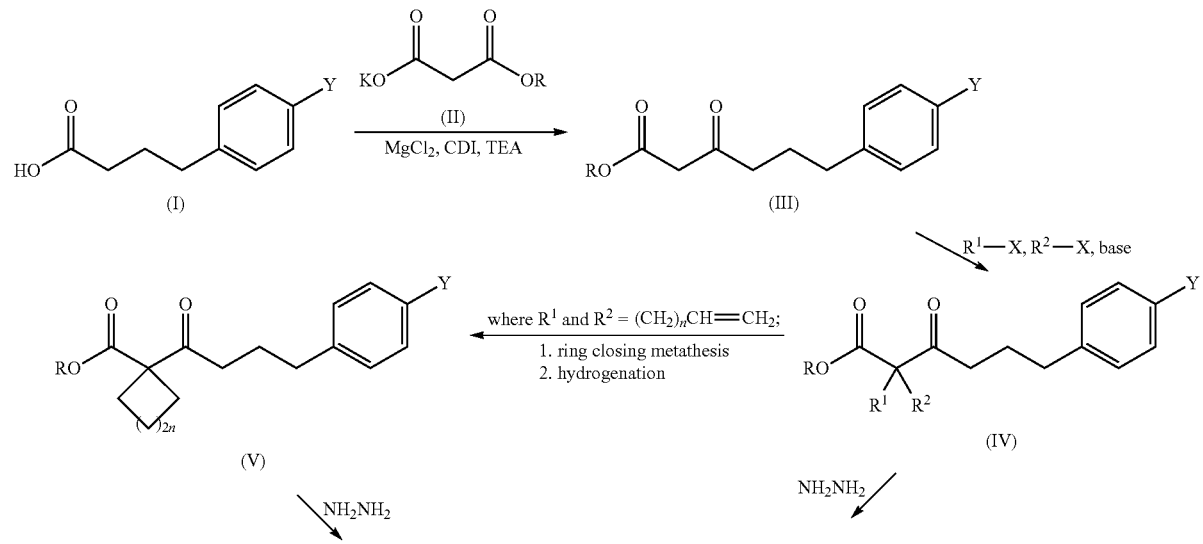

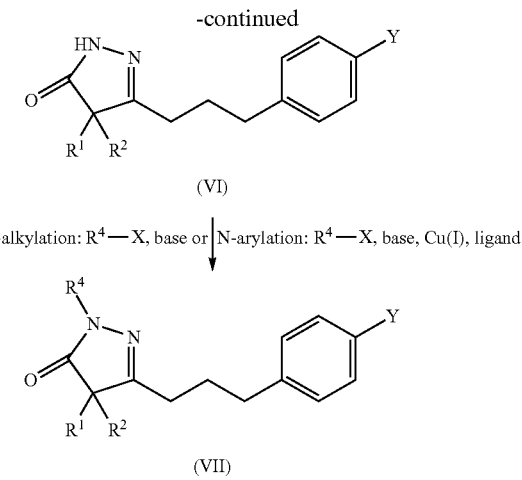

(VI)

N-alkylation: $R^4$—X, base or | N-arylation: $R^4$—X, base, Cu(I), ligand (VII)

Functionalization of pyrazalone VII can also be readily achieved (Scheme 2). In instances where Y is OH, O-alkylation can be conveniently accomplished by reacting VII with, for example, an activated halide such as VIII in the presence of an appropriate base such as $Cs_2CO_3$, NaOEt, NaH, or the like. The resulting fibrate ester IX can then be hydrolyzed to deliver the corresponding acid X. The acid can be further coupled with an amine (to give amide XI) or a sulfonamide (to deliver acyl sulfonamide XII) via the use of an appropriate coupling reagent such as HATU, EEDQ, EDC, CDI, or the like, and in the presence of an appropriate base such as TEA, Hunig's base, DABCO, DMAP, or the like. Alternatively, acid X could be reduced to its corresponding alcohol XIV, by its initial conversion to the mixed anhydride XIII and subsequent treatment with agents such as sodium borohydride, lithium borohydride, or the like. In turn, primary alcohol XIV can be converted to the secondary alcohol XV via a two-step protocol: (1) oxidation with reagents such as Dess-Martin periodinane, $SO_3$-pyridine, Swern reagent, or the like, and (2) reaction with a suitable organometallic reagent depicted generically as $R^8$-M. A subsequent oxidative event would deliver ketone XVI. Alternatively, alcohol XIV can be transformed to amine XVII using a variety of approaches known to those skilled in the art (e.g. the palladium-mediated reduction of an intermediate azide accessed using Curtius rearrangement). Further derivatization of amine XVII to amide XVIII (via, for example, acylation with $R^8$—C(=O)Cl) or to sulfonamide XIX (via, for example, sulfonylation with $R^8$—S(=O)$_2$Cl) could also be carried out using standard procedures known to those skilled in the art. In instance were Y is Cl, Br, or I (Scheme 2), metal-catalyzed cross-couplings such as the Suzuki reaction, the Stille reaction, the Negishi reaction, or the like, can be employed to facilitate further structural diversification from pyrazole VII. Once again, manipulations of the functional groups on biaryl XX (denoted generically as FG in Scheme 2) using some of, but not limited to, the chemical transformations described previously (i.e. acylation, sulfonylation, oxidation, reduction, alkylation, arylation, hydrolysis, addition or the like), can be readily envisioned.

Scheme 2

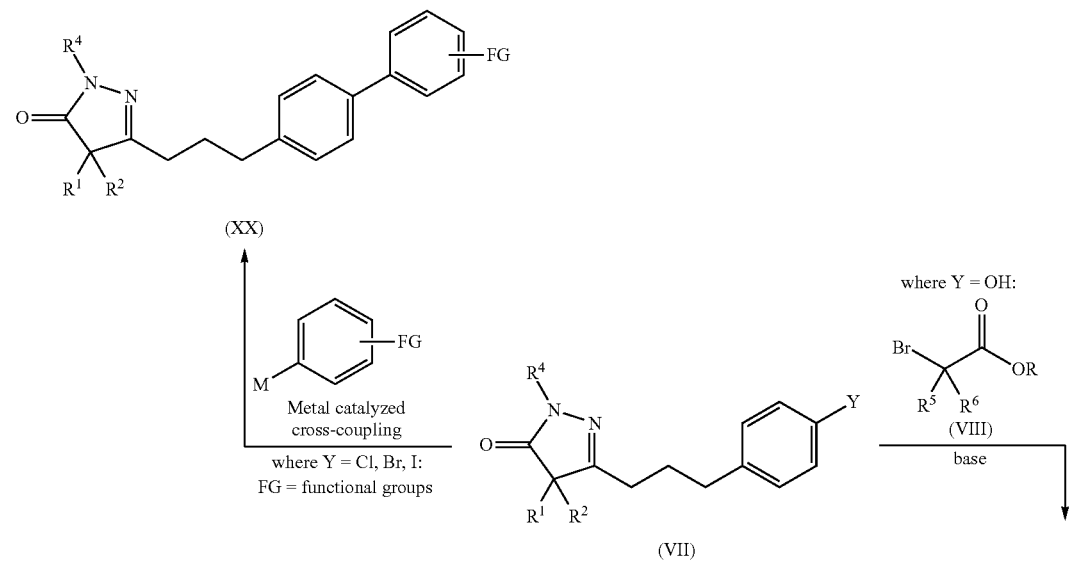

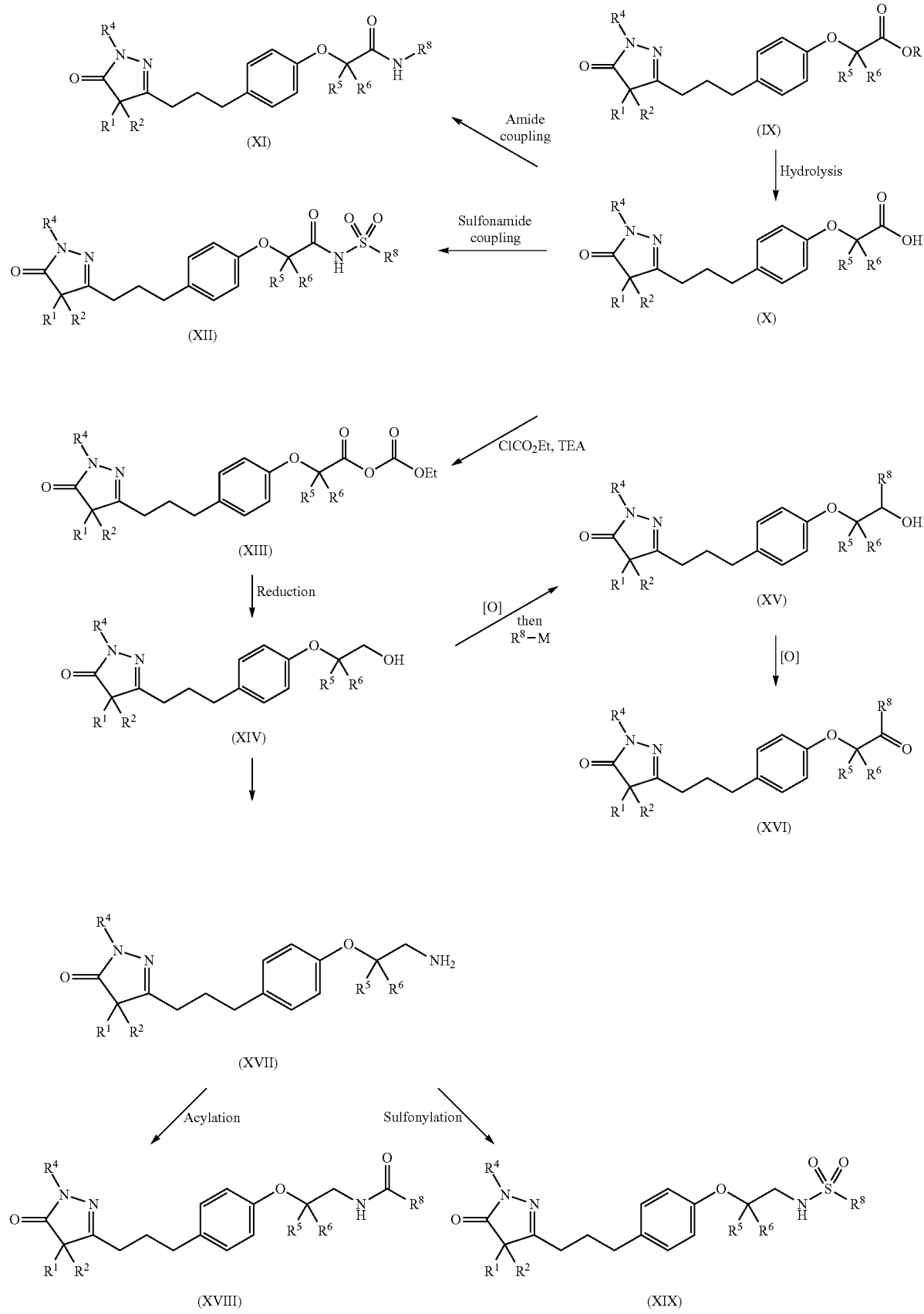

Example 1: 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid

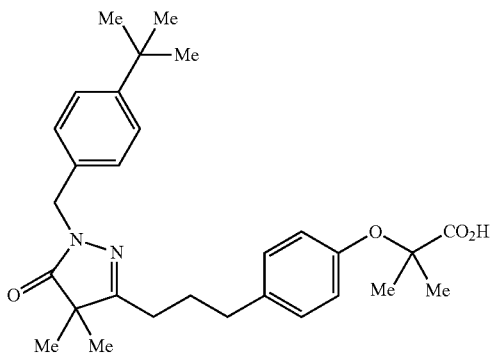 [SMILES: CC(C)(Oc1ccc(CCCC2=NN(Cc3ccc(C(C)(C)C)cc3)C(=O)C2(C)C)cc1)C(=O)O]

Step 1: To an ethanol solution (0.8 M) of 4-(4-hydroxyphenyl)butanoic acid (1 eq.) was added freshly prepared sodium ethoxide (2 eq.). The resulting mixture was then heated at reflux for 30 min before ethyl 2-bromo-2-methylpropanoate (3 eq.) was added neat and dropwise over 5 min. The now black reaction suspension was heated at reflux for another 2 h before another portion of sodium ethoxide (1 eq.) was added. The resulting mixture was then heated at reflux for 16 h before it was carefully quenched with the addition of 10% aq. HCl. After the removal of the volatiles in vacuo, the resulting brown oil was partitioned between EtOAc and water. The aqueous wash was separated and back-extracted with EtOAc. The combined organic extracts were washed further with water and brine, dried over $Na_2SO_4$, filtered and the filtrate concentrated in vacuo. Trituration of the crude product thus obtained in hexanes afforded the desired product as a tan solid (85% yield).

Step 2: To an acetonitrile solution (0.05 M) of 4-(4-((1-ethoxy-2-methyl-1-oxopropan-2-yl)oxy)phenyl)butanoic acid (1 eq.) from the previous step was added CDI (1.1 eq.). The resulting yellow solution was then allowed to stir at RT for 2.5 h before it was added dropwise, over a period of 1.5 h, into a white suspension of potassium 3-methoxy-3-oxopropanoate (2.1 eq.), magnesium chloride (2.5 eq.) and triethylamine (3.2 eq.). The resulting suspension was then stirred at RT for 16 h and finally heated at reflux for another 24 h. The crude reaction suspension thus obtained was cooled to RT and diluted with EtOAc. The insolubles were then removed via filtration and rinsed further with EtOAc and DCM. The filtrate thus obtained was concentrated in vacuo, re-taken up in EtOAc and washed sequentially with 10% aq. HCl, water and brine. The organic extract was then dried over $Na_2SO_4$ and filtered. Concentration of the filtrate in vacuo afford the desired product as a golden oil (96% yield) which can be used without further purification.

Step 3: To a DMSO solution (0.1 M) of methyl 6-(4-((1-ethoxy-2-methyl-1-oxopropan-2-yl)oxy)phenyl)-3-oxohexanoate (1 eq.) from the previous step was added cesium carbonate (3 eq.) and iodomethane (3 eq.). The resulting mixture was then allowed to stir at RT for 16 h. The crude reaction mixture thus obtained was diluted with ether and washed sequentially with cold water, 10% aq. HCl, 1 N aq. NaOH, water and finally brine. The organic extract was then dried over $Na_2SO_4$, filtered and the filtrate concentrated in vacuo. Purification of the crude product thus obtained by way of column chromatography ($SiO_2$, gradient elution, 9:1→3:7 (v/v) Hex: EtOAc) afforded the desired product as a colorless oil (74% yield).

Step 4: To an ethanol solution (0.7 M) of methyl 6-(4-((1-ethoxy-2-methyl-1-oxopropan-2-yl)oxy)phenyl)-2,2-dimethyl-3-oxohexanoate (1 eq.) from the previous step was added hydrazine monohydrate (1.5 eq.). The reaction vessel was then tightly sealed and heated at 80° C. behind a blast shield for 48 h. After cooling to RT, the volatiles were then removed in vacuo and the resulting residue was partitioned between ether and 10% aq. HCl. The aqueous layer was separated and back-extracted with ether. The combined organic extracts were then washed further with water and brine, dried over $Na_2SO_4$ and filtered. Concentration for the filtrate in vacuo afforded the desired product as a colorless oil (82% yield).

Step 5: To an acetonitrile solution (0.15 M) of ethyl 2-(4-(3-(4,4-dimethyl-5-oxo-4,5-dihydro-1H-pyrazol-3-yl)propyl)phenoxy)-2-methylpropanoate (1 eq.) from the previous step was added 4-tert-butylbenzyl bromide (1.2 eq.) and cesium carbonate (3 eq.). The resulting mixture was then heated at 60° C. for 16 h. After cooling the reaction suspension to RT, the reaction was carefully quenched with 10% aq. HCl and extracted with ether. The combined organic extracts were then washed further with water and brine, dried over $Na_2SO_4$, filtered and the filtrate concentrated in vacuo. Purification of the crude product thus obtained by way of column chromatography ($SiO_2$, gradient elution, 9:1→3:7 (v/v) Hex: EtOAc) afforded the desired product as a colorless oil (85% yield).

Step 6: To a 2:1 (v/v) THF: MeOH solution (0.13 M) of ethyl 2-(4-(3-(1-(4-(tert-butyl)benzyl)-4,4-dimethyl-5-oxo-4,5-dihydro-1H-pyrazol-3-yl)propyl)phenoxy)-2-methylpropanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with EtOAc. The combined organic extracts were then washed further with water and brine, dried over $Na_2SO_4$, filtered and the filtrate concentrated in vacuo. Trituration of the crude product thus obtained in hexanes afforded the title compound as a white solid (96% yield). LC-MS: 479 $(M+H)^+$.

Example 2: 2-(4-(3-(1-(4-(tert-butyl)benzyl)-4,4-dimethyl-5-oxo-4,5-dihydro-1H-pyrazol-3-yl)propyl)phenoxy)-2-methyl-N-(phenylsulfonyl)propanamide

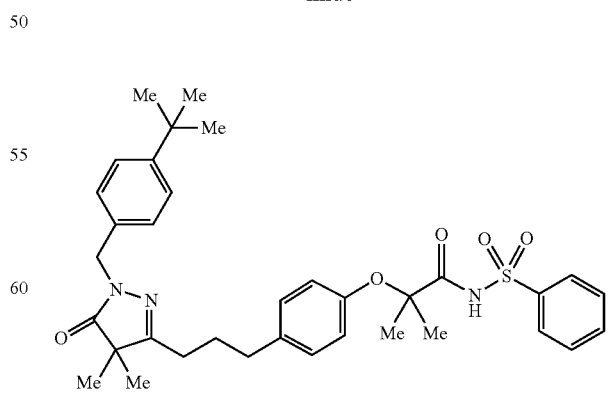

To a dichloromethane solution (0.1 M) of 2-(4-(3-(1-(4-(tert-butyl)benzyl)-4,4-dimethyl-5-oxo-4,5-dihydro-1H- pyrazol-3-yl)propyl)phenoxy)-2-methylpropanoic acid (1 eq., Example 1) was added phenyl sulfonamide (1.4 eq.) and DMAP (1 eq.). The resulting mixture was sonicated briefly (~5 min) before EDC (1.4 eq.) was added neat and in one rapid portion. After 72 h, the volatiles were removed in vacuo and the resulting residue thus obtained was directly subjected to purification by way of reverse phase column chromatography ($C_{18}$, gradient elution, 9:1 (v/v) $H_2O$: MeCN+0.1% TFA→MeCN+0.1% TFA) to furnish the title product as a white solid (42% yield). LC-MS: 618 (M+H)+.

Example 3: N-benzyl-2-(4-(3-(1-(4-(tert-butyl)benzyl)-4,4-dimethyl-5-oxo-4,5-dihydro-1H-pyrazol-3-yl)propyl)phenoxy)-2-methylpropanamide

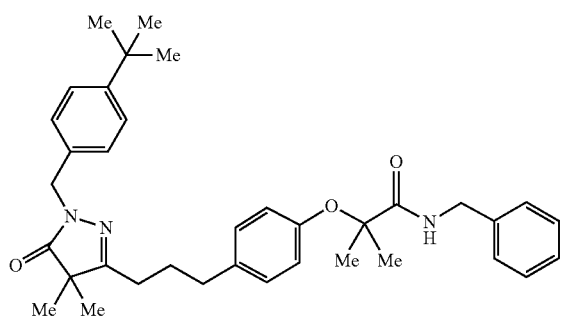 [SMILES: CC(C)(Oc1ccc(CCCC2=NN(Cc3ccc(C(C)(C)C)cc3)C(=O)C2(C)C)cc1)C(=O)NCc1ccccc1]

To a DMF solution (0.1 M) of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid (1 eq., Example 1) was added benzylamine (1 eq.) and HATU (1.2 eq.). The resulting solution was sonicated briefly (~5 min) before Hunig's base (1.5 eq.) was added neat and in one rapid portion. After 5 h, the reaction mixture was diluted with ether and washed sequentially with water, 10% aq. HCl, 1 N aq. NaOH and brine. The organic extract was then dried over $Na_2SO_4$, filtered and the filtrate concentrated in vacuo. Purification of the crude product thus obtained by way of column chromatography ($SiO_2$, gradient elution, 9:1→3:7 (v/v) Hex:EtOAc) afforded the title compound as a colorless oil (88% yield). LC-MS: 568 (M+H)+.

Example 4: 2-(4-(3-(1-(4-(tert-butyl)benzyl)-4,4-dimethyl-5-oxo-4,5-dihydro-1H-pyrazol-3-yl)propyl)phenoxy)-2-methyl-N-(pyridin-2-ylmethyl)propanamide

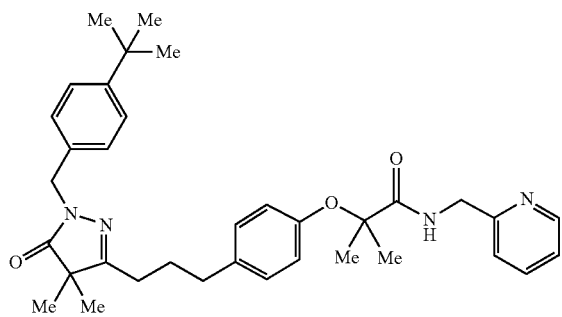 [SMILES: CC(C)(Oc1ccc(CCCC2=NN(Cc3ccc(C(C)(C)C)cc3)C(=O)C2(C)C)cc1)C(=O)NCc1ccccn1]

Prepared in an analogous manner to Example 3 but using pyridin-2-ylmethanamine in place of benzylamine as the amine coupling partner. LC-MS: 569 (M+H)+.

Example 5: 2-(4-(3-(1-(4-(tert-butyl)benzyl)-4,4-dimethyl-5-oxo-4,5-dihydro-1H-pyrazol-3-yl)propyl)phenoxy)-2-methyl-N-(pyridin-4-ylmethyl)propanamide

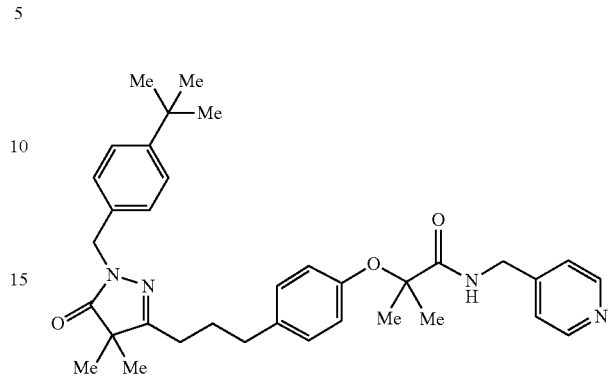

Prepared in an analogous manner to Example 3 but using pyridin-4-ylmethanamine in place of benzylamine as the amine coupling partner. LC-MS: 569 (M+H)+.

Example 6: 2-(4-(3-(1-(4-(tert-butyl)benzyl)-4,4-dimethyl-5-oxo-4,5-dihydro-1H-pyrazol-3-yl)propyl)phenoxy)-N-(cyclohexylmethyl)-2-methylpropanamide

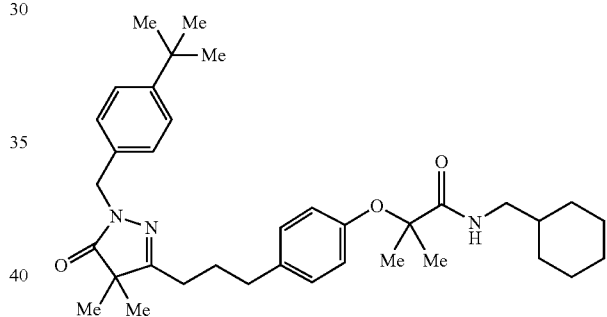

Prepared in an analogous manner to Example 3 but using cyclohexylamine in place of benzylamine as the amine coupling partner. LC-MS: 574 (M+H)+.

Example 7: 2-(4-(3-(4,4-dimethyl-5-oxo-1-(3-(trifluoromethyl)benzyl)-4,5-dihydro-1H-pyrazol-3-yl)propyl)phenoxy)-2-methylpropanoic acid

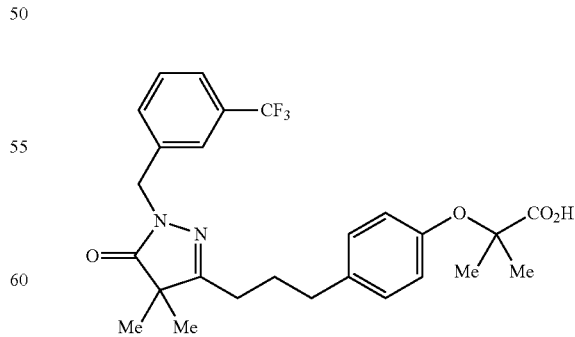

Prepared in an analogous manner to Example 1 but using 3-(trifluoromethyl)benzyl bromide in place of 4-tert-butylbenzyl bromide as the electrophile in step 5. LC-MS: 491 (M+H)+.

Example 8: 2-(4-(3-(4,4-dimethyl-5-oxo-1-(4-(trifluoromethyl)benzyl)-4,5-dihydro-1H-pyrazol-3-yl)propyl)phenoxy)-2-methylpropanoic acid

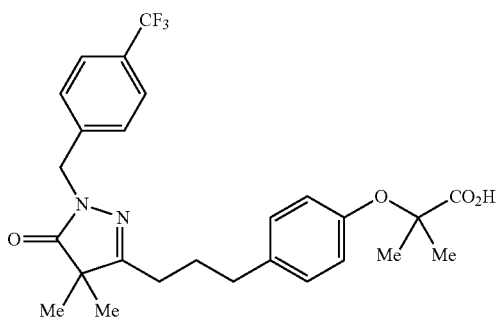 [SMILES: CC(C)(Oc1ccc(CCCC2=NN(Cc3ccc(C(F)(F)F)cc3)C(=O)C2(C)C)cc1)C(=O)O]

Prepared in an analogous manner to Example 1 but using 4-(trifluoromethyl)benzyl bromide in place of 4-tert-butylbenzyl bromide as the electrophile in step 5. LC-MS: 491 (M+H)$^+$.

Example 9: 2-(4-(3-(4,4-dimethyl-5-oxo-1-phenethyl-4,5-dihydro-H-pyrazol-3-yl)propyl)phenoxy)-2-methylpropanoic acid

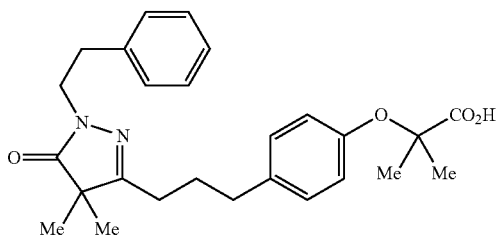 [SMILES: CC(C)(Oc1ccc(CCCC2=NN(CCc3ccccc3)C(=O)C2(C)C)cc1)C(=O)O]

Prepared in an analogous manner to Example 1 but using 2.8 eq. of (2-bromoethyl)benzene in place of 4-tert-butylbenzyl bromide as the electrophile in step 5. LC-MS: 437 (M+H)$^+$.

Example 10: 2-(4-(3-(4,4-dimethyl-5-oxo-1-phenyl-4,5-dihydro-1H-pyrazol-3-yl)propyl)phenoxy)-2-methylpropanoic acid

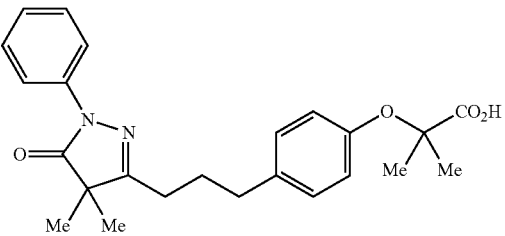 [SMILES: CC(C)(Oc1ccc(CCCC2=NN(c3ccccc3)C(=O)C2(C)C)cc1)C(=O)O]

Step 1: To a DMSO solution (0.13 M) of ethyl 2-(4-(3-(4,4-dimethyl-5-oxo-4,5-dihydro-1H-pyrazol-3-yl)propyl)phenoxy)-2-methylpropanoate (1 eq., Example 1, Step 4) was added iodobenzene (1.5 eq.), copper(I) iodide (0.1 eq.), L-proline (0.2 eq.) and potassium carbonate (2.5 eq.). The resulting suspension was then deoxygenated via sub-surface purging with a stream of nitrogen for 15 min. Then, the reaction vessel was tightly sealed and the reaction mixture was heated at 95° C. for 16 h. After cooling the reaction suspension to RT, the reaction was carefully quenched with 10% aq. HCl and extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, gradient elution, 9:1→1:1 (v/v) Hex: EtOAc) afforded the desired product as a pale yellow oil that solidified upon standing (76% yield).

Step 2: To a 2:1 (v/v) THF: MeOH solution (0.05 M) of ethyl 2-(4-(3-(4,4-dimethyl-5-oxo-1-phenyl-4,5-dihydro-1H-pyrazol-3-yl)propyl)phenoxy)-2-methylpropanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with ether and EtOAc. The combined organic extracts were then washed further with water and brine, dried over Na$_2$SO$_4$, filtered and the filtrate concentrated in vacuo. Trituration of the crude product thus obtained in hexanes afforded the title compound as a white solid (99% yield). LC-MS: 409 (M+H)$^+$.

Example 11: 2-(4-(3-(1-(4-(tert-butyl)phenyl)-4,4-dimethyl-5-oxo-4,5-dihydro-1H-pyrazol-3-yl)propyl)phenoxy)-2-methylpropanoic acid

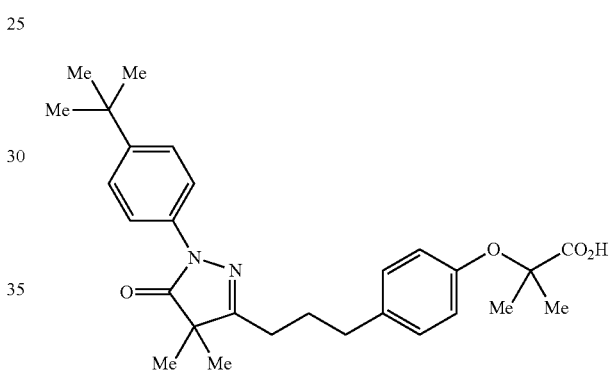

Prepared in an analogous manner to Example 10 but using 1-(tert-butyl)-4-iodobenzene in place of iodobenzene as the aryl iodide coupling partner in step 1. LC-MS: 465 (M+H)$^+$.

Example 12: 2-(4-(3-(1-(4-isopropylbenzyl)-4,4-dimethyl-5-oxo-4,5-dihydro-1H-pyrazol-3-yl)propyl)phenoxy)-2-methylpropanoic acid

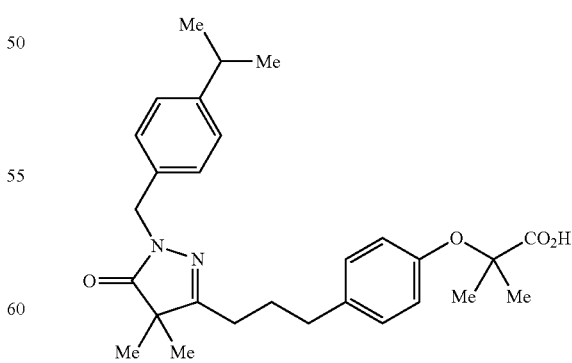

Prepared in an analogous manner to Example 1 but using 1-(bromomethyl)-4-isopropylbenzene in place of 4-tert-butylbenzyl bromide as the electrophile in step 5. LC-MS: 465 (M+H)$^+$.

Example 13: 2-(4-(3-(1-(4-bromobenzyl)-4,4-dimethyl-5-oxo-4,5-dihydro-1H-pyrazol-3-yl)propyl)phenoxy)-2-methylpropanoic acid

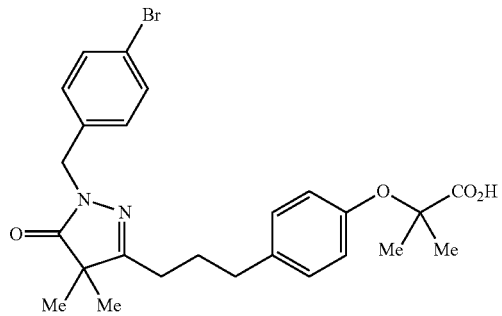 [SMILES: CC(C)(Oc1ccc(CCCC2=NN(Cc3ccc(Br)cc3)C(=O)C2(C)C)cc1)C(=O)O]

Step 1: To an acetonitrile solution (0.07 M) of ethyl 2-(4-(3-(4,4-dimethyl-5-oxo-4,5-dihydro-1H-pyrazol-3-yl)propyl)phenoxy)-2-methylpropanoate (1 eq., Example 1, Step 4) was added 4-bromobenzyl bromide (1.2 eq.) and cesium carbonate (3 eq.). The resulting mixture was then heated at 60° C. for 16 h. After cooling the reaction suspension to RT, the reaction was carefully quenched with 10% aq. HCl and extracted with ether. The combined organic extracts were then washed further with water and brine, dried over $Na_2SO_4$, filtered and the filtrate concentrated in vacuo. Purification of the crude product thus obtained by way of column chromatography ($SiO_2$, gradient elution, 9:1→3:7 (v/v) Hex: EtOAc) afforded the desired product as a colorless oil (82% yield).

Step 2: To a 2:1 (v/v) THF: MeOH solution (0.05 M) of ethyl 2-(4-(3-(1-(4-bromobenzyl)-4,4-dimethyl-5-oxo-4,5-dihydro-1H-pyrazol-3-yl)propyl)phenoxy)-2-methylpropanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with ether and EtOAc. The combined organic extracts were then washed further with water and brine, dried over $Na_2SO_4$, filtered and the filtrate concentrated in vacuo. Trituration of the crude product thus obtained in hexanes afforded the title compound as a white solid (99% yield). LC-MS: 501. 503 (M+H)$^+$.

Example 14: 2-(4-(3-(1-([1,1'-biphenyl]-4-ylmethyl)-4,4-dimethyl-5-oxo-4,5-dihydro-1H-pyrazol-3-yl)propyl)phenoxy)-2-methylpropanoic acid

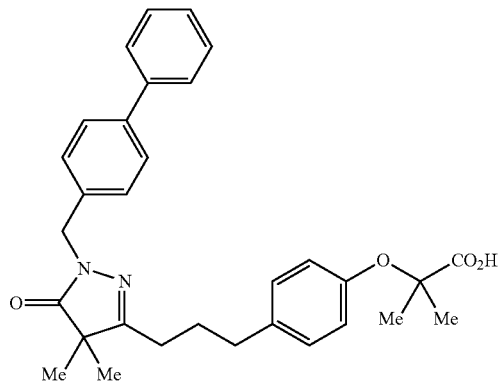 [SMILES: CC(C)(Oc1ccc(CCCC2=NN(Cc3ccc(-c4ccccc4)cc3)C(=O)C2(C)C)cc1)C(=O)O]

Step 1: To a 3:1 (v/v) DME: water solution (0.03 M) of ethyl 2-(4-(3-(1-(4-bromobenzyl)-4,4-dimethyl-5-oxo-4,5-dihydro-1H-pyrazol-3-yl)propyl)phenoxy)-2-methylpropanoate (1 eq., Example 13, Step 1) was added phenylboronic acid (1.2 eq.), tetrakis(triphenylphosphine)palladium (0) (0.1 eq.) and potassium carbonate (3 eq.). The resulting biphasic mixture was deoxygenated via sub-surface purging with a stream of nitrogen for 15 min. Then, the reaction vessel was tightly sealed and the reaction mixture was heated at 90° C. for 16 h. After cooling the reaction suspension to RT, the reaction was carefully quenched with 10% aq. HCl and extracted with ether. The combined organic extracts were then washed further with water and brine, dried over $Na_2SO_4$, filtered and the filtrate concentrated in vacuo. Purification of the crude product thus obtained by way of column chromatography ($SiO_2$, gradient elution, 9:1→3:7 (v/v) Hex: EtOAc) afforded the desired product as a pale yellow oil (61% yield).

Step 2: To a 2:1 (v/v) THF: MeOH solution (0.05 M) of ethyl 2-(4-(3-(1-([1,1'biphenyl]-4-ylmethyl)-4,4-dimethyl-5-oxo-4,5-dihydro-1H-pyrazol-3-yl)propyl)phenoxy)-2-methylpropanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with ether and EtOAc. The combined organic extracts were then washed further with water and brine, dried over $Na_2SO_4$, filtered and the filtrate concentrated in vacuo. Trituration of the crude product thus obtained in hexanes afforded the title compound as a white solid (95% yield). LC-MS: 499 (M+H)$^+$.

Example 15: 2-(4-(3-(4,4-dimethyl-5-oxo-1-((2',3',4',5'-tetrahydro-[1,1'-biphenyl]-4-yl)methyl)-4,5-dihydro-1H-pyrazol-3-yl)propyl)phenoxy)-2-methylpropanoic acid

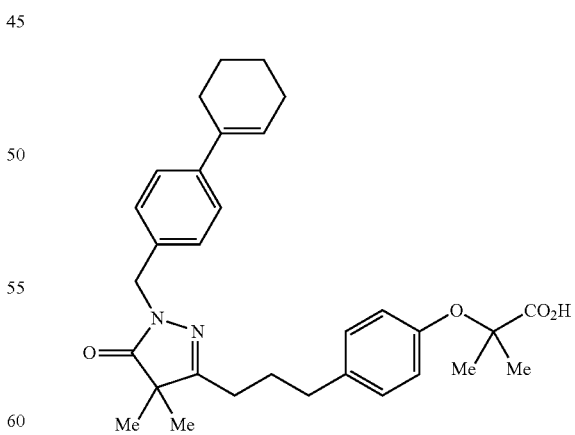

Prepared in an analogous manner to Example 14 but using 1-cyclohexen-1-ylboronic acid, pinacol ester in place of phenylboronic acid as the coupling partner in step 1. LC-MS: 503 (M+H)$^+$.

Example 16: 2-(4-(3-(1-(4-cyclopropylbenzyl)-4,4-dimethyl-5-oxo-4,5-dihydro-1H-pyrazol-3-yl)propyl)phenoxy)-2-methylpropanoic acid

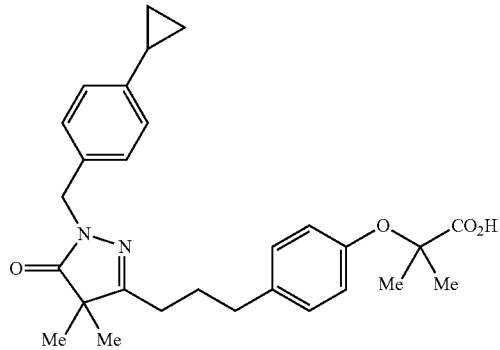 [SMILES: CC(C)(Oc1ccc(CCCC2=NN(Cc3ccc(C4CC4)cc3)C(=O)C2(C)C)cc1)C(=O)O]

Prepared in an analogous manner to Example 14 but using palladium(II) acetate (0.1 eq.) and tricyclohexylphosphine (0.2 eq.) in place of tetrakis(triphenylphosphine)palladium (0) as the catalyst system, cyclopropylboronic acid (5 eq.) in place of phenylboronic acid as the coupling partner, potassium phosphate (3.5 eq.) in place of potassium carbonate as the base, and toluene in place of DME as the reaction co-solvent in step 1. LC-MS: 463 (M+H)$^+$.

Example 17: 2-(4-(3-(1-(4-cyclohexylbenzyl)-4,4-dimethyl-5-oxo-4,5-dihydro-1H-pyrazol-3-yl)propyl)phenoxy)-2-methylpropanoic acid

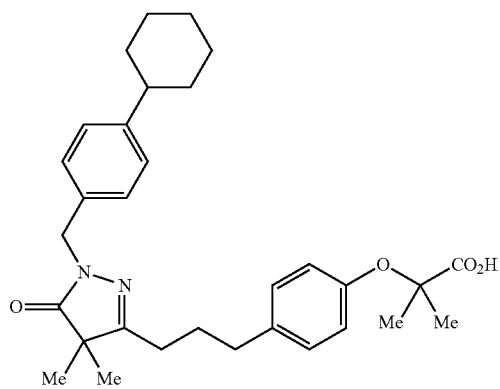 [SMILES: CC(C)(Oc1ccc(CCCC2=NN(Cc3ccc(C4CCCCC4)cc3)C(=O)C2(C)C)cc1)C(=O)O]

To an ethanol solution (0.01 M) of 2-(4-(3-(4,4-dimethyl-5-oxo-1-((2',3',4',5'-tetrahydro-[1,1'-biphenyl]-4-yl)methyl)-4,5-dihydro-H-pyrazol-3-yl)propyl)phenoxy)-2-methylpropanoic acid (1 eq., Example 15) was added palladium black (0.1 eq., 10% w/w (dry) over carbon). The resulting suspension was evacuated and back-filled with hydrogen gas (50 psi, 3×). Then, the reaction mixture was shaken on a Parr hydrogenator under 50 psi of hydrogen for 16 h. The mixture was carefully quenched with DCM and filtered through a bed of DCM-wetted celite. The insolubles were then washed further with DCM and EtOAc. Concentration of the filtrate thus obtained in vacuo furnished the title compound as a white solid (70% yield). LC-MS: 505 (M+H)$^+$.

Example 18: 2-(4-(3-(1-(3-fluoro-4-(trifluoromethyl)benzyl)-4,4-dimethyl-5-oxo-4,5-dihydro-1H-pyrazol-3-yl)propyl)phenoxy)-2-methylpropanoic acid

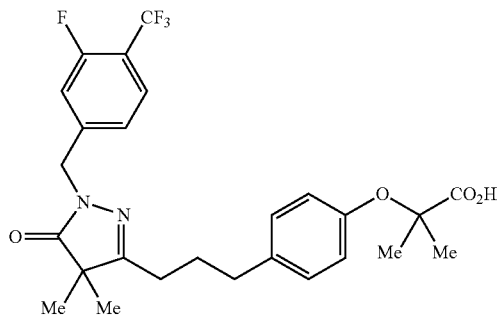 [SMILES: CC(C)(Oc1ccc(CCCC2=NN(Cc3ccc(C(F)(F)F)c(F)c3)C(=O)C2(C)C)cc1)C(=O)O]

Prepared in an analogous manner to Example 1 but using 3-fluoro-4-(trifluoromethyl)benzyl bromide in place of 4-tert-butylbenzyl bromide as the electrophile in step 5. LC-MS: 509 (M+H)$^+$.

Example 19: 2-(4-(3-(4,4-dimethyl-5-oxo-1-(4-(trifluoromethyl)phenyl)-4,5-dihydro-1H-pyrazol-3-yl)propyl)phenoxy)-2-methylpropanoic acid

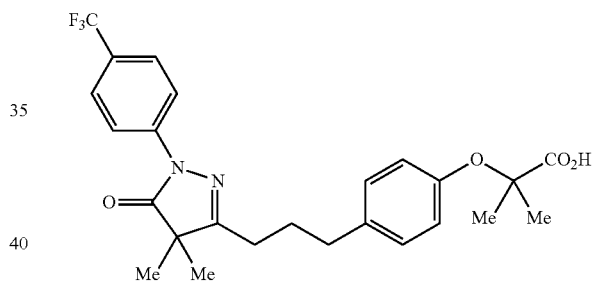

Prepared in an analogous manner to Example 10 but using 4-iodobenzotrifluoride in place of iodobenzene as the aryl iodide coupling partner in step 1. LC-MS: 477 (M+H)$^+$.

Example 20: 2-(4-(3-(4,4-dimethyl-5-oxo-1-(3-(trifluoromethyl)phenyl)-4,5-dihydro-1H-pyrazol-3-yl)propyl)phenoxy)-2-methylpropanoic acid

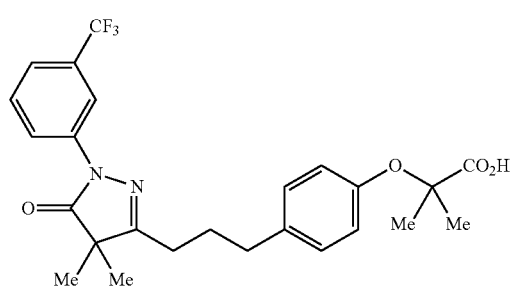 [SMILES: CC(C)(Oc1ccc(CCCC2=NN(c3cccc(C(F)(F)F)c3)C(=O)C2(C)C)cc1)C(=O)O]

Prepared in an analogous manner to Example 10 but using 3-iodobenzotrifluoride in place of iodobenzene as the aryl iodide coupling partner in step 1. LC-MS: 477 (M+H)$^+$.

Example 21: 2-(4-(3-(4,4-dimethyl-5-oxo-1-(5-(trifluoromethyl)pyridin-2-yl)-4,5-dihydro-1H-pyrazol-3-yl)propyl)phenoxy)-2-methylpropanoic acid

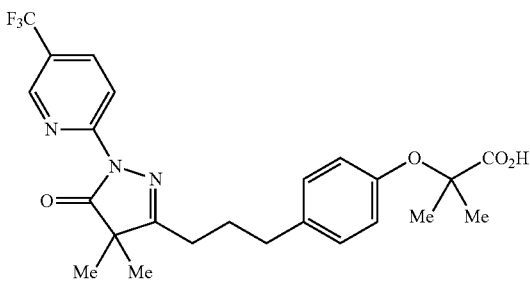 [SMILES: CC(C)(Oc1ccc(CCCC2=NN(c3ccc(C(F)(F)F)cn3)C(=O)C2(C)C)cc1)C(=O)O]

Prepared in an analogous manner to Example 10 but using 2-iodo-5-(trifluoromethyl)pyridine in place of iodobenzene as the aryl iodide coupling partner in step 1. LC-MS: 478 (M+H)$^+$.

Example 22: 2-(4-(3-(4,4-dimethyl-5-oxo-1-(4-(trifluoromethyl)phenyl)-4,5-dihydro-1H-pyrazol-3-yl)propyl)phenoxy)-2-methyl-N-(phenylsulfonyl)propanamide

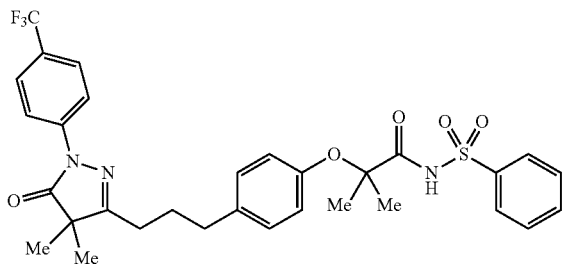 [SMILES: CC(C)(Oc1ccc(CCCC2=NN(c3ccc(C(F)(F)F)cc3)C(=O)C2(C)C)cc1)C(=O)NS(=O)(=O)c1ccccc1]

Prepared in an analogous manner to Example 2 but using 2-(4-(3-(4,4-dimethyl-5-oxo-1-(4-(trifluoromethyl)phenyl)-4,5-dihydro-1H-pyrazol-3-yl)propyl)phenoxy)-2-methylpropanoic acid (Example 19) in place of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid as the coupling partner. LC-MS: 616 (M+H)$^+$.

Example 23: 2-(4-(3-(3-(4-(tert-butyl)benzyl)-4-oxo-2,3-diazaspiro[4,4]non-1-en-1-yl)propyl)phenoxy)-2-methylpropanoic acid

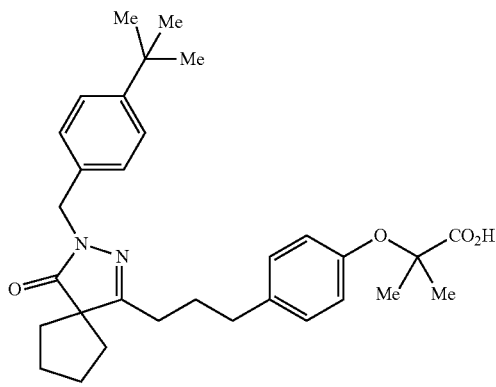 [SMILES: CC(C)(Oc1ccc(CCCC2=NN(Cc3ccc(C(C)(C)C)cc3)C(=O)C23CCCC3)cc1)C(=O)O]

Step 1: To a DMSO solution (0.1 M) of methyl 6-(4-((1-ethoxy-2-methyl-1-oxopropan-2-yl)oxy)phenyl)-3-oxohexanoate (1 eq., Example 1, Step 2) was added cesium carbonate (3 eq.) and allyl bromide (3 eq.). The resulting mixture was then allowed to stir at RT for 16 h. The crude reaction mixture thus obtained was diluted with ether and washed sequentially with cold water, 10% aq. HCl, 1 N aq. NaOH, water and finally brine. The organic extract was then dried over Na$_2$SO$_4$, filtered and the filtrate concentrated in vacuo. Purification of the crude product thus obtained by way of column chromatography (SiO$_2$, gradient elution, 9:1→1:1 (v/v) Hex: EtOAc) afforded the desired product as a colorless oil (62% yield).

Step 2: To a freshly deoxygenated 1,2-dichloroethane solution (0.002 M) of methyl 2,2-diallyl-6-(4-((1-ethoxy-2-methyl-1-oxopropan-2-yl)oxy)phenyl)-3-oxohexanoate (1 eq.) from the previous step was added Grubb's catalyst, second generation (0.05 eq.). The resulting mixture was then allowed to stir at RT, with a vent to allow for the outgassing of ethylene produced, for 16 h. The volatiles were then removed in vacuo and the resulting green residue was directly subjected to purification by way of column chromatography (SiO$_2$, gradient elution, 9:1-1:1 (v/v) Hex: EtOAc) to furnish the desired product as a colorless oil (89% yield).

Step 3: To an ethyl acetate solution (0.07 M) of methyl 1-(4-(4-((1-ethoxy-2-methyl-1-oxopropan-2-yl)oxy)phenyl)butanoyl)cyclopent-3-enecarboxylate (1 eq.) from the previous step was added palladium black (0.1 eq., 10% w/w (wet) over carbon). The resulting suspension was evacuated and back-filled with hydrogen gas (3×). Then, the reaction mixture was stirred under a static hydrogen atmosphere maintained with a balloon for 16 h. The mixture was carefully quenched with DCM and filtered through a bed of DCM-wetted celite. The insolubles were then washed further with DCM. Concentration of the filtrate thus obtained in vacuo furnished the desired compound as a colorless oil (94% yield).

Step 4: To an ethanol solution (0.18 M) of methyl 1-(4-(4-((1-ethoxy-2-methyl-1-oxopropan-2-yl)oxy)phenyl)butanoyl)cyclopentanecarboxylate (1 eq.) from the previous step was added hydrazine monohydrate (1.5 eq.). The reaction vessel was then tightly sealed and heated at 80° C. behind a blast shield for 96 h. After cooling to RT, the volatiles were then removed in vacuo and the resulting residue was partitioned between ether and 10% aq. HCl. The aqueous layer was separated and back-extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, gradient elution, 9:1→3:7 (v/v) Hex: EtOAc) afforded the desired product as a colorless oil that solidified upon standing (70% yield).

Step 5: To an acetonitrile solution (0.16 M) of ethyl 2-methyl-2-(4-(3-(4-oxo-2,3-diazaspiro[4,4]non-1-en-1-yl)propyl)phenoxy)propanoate (1 eq.) from the previous step was added 4-tert-butylbenzyl bromide (1.2 eq.) and cesium carbonate (3 eq.). The resulting mixture was then heated at 60° C. for 16 h. After cooling the reaction suspension to RT, the reaction was carefully quenched with 10% aq. HCl and extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, gradient elution, Hex→1:1 (v/v) Hex: EtOAc) afforded the desired product as a pale yellow oil (96% yield).

Step 6: To a 2:1 (v/v) THF: MeOH solution (0.15 M) of ethyl 2-(4-(3-(3-(4-(tert-butyl)benzyl-4-oxo-2,3-diazaspiro [4,4]non-1-en-1-yl)propyl)phenoxy)-2-methylpropanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with ether. The combined organic extracts were then washed further with water and brine, dried over Na$_2$SO$_4$, filtered and the filtrate concentrated in vacuo. Trituration of the crude product thus obtained in hexanes afforded the title compound as a white solid (85% yield). LC-MS: 505 (M+H)$^+$.

Example 24: 2-methyl-2-(4-(3-(4-oxo-3-(4-(trifluoromethyl)phenyl)-2,3-diazaspiro[4,4]non-1-en-1-yl) propyl)phenoxy)propanoic acid

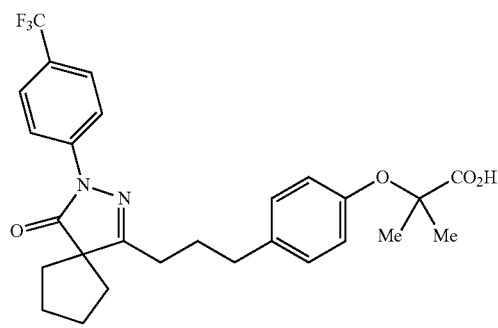 [SMILES: CC(C)(Oc1ccc(CCCC2=NN(c3ccc(C(F)(F)F)cc3)C(=O)C23CCCC3)cc1)C(=O)O]

Prepared in an analogous manner to Example 10 but using 4-iodobenzotrifluoride in place of iodobenzene, and ethyl 2-methyl-2-(4-(3-(4-oxo-2,3-diazaspiro[4,4]non-1-en-1-yl) propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 503 (M+H)$^+$.

Example 25: 2-methyl-2-(4-(3-(4-oxo-3-(4-(trifluoromethyl)phenyl)-2,3-diazaspiro[4,4]non-1-en-1-yl) propyl)phenoxy)-N-(phenylsulfonyl)propanamide

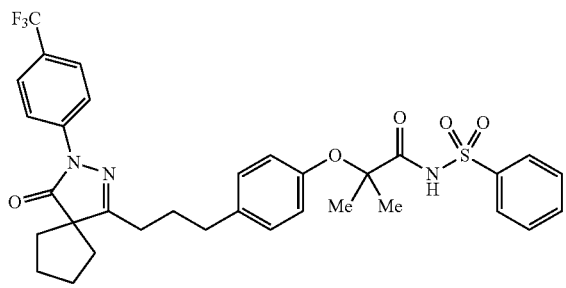 [SMILES: CC(C)(Oc1ccc(CCCC2=NN(c3ccc(C(F)(F)F)cc3)C(=O)C23CCCC3)cc1)C(=O)NS(=O)(=O)c1ccccc1]

Prepared in an analogous manner to Example 2 but using 2-methyl-2-(4-(3-(4-oxo-3-(4-(trifluoromethyl)phenyl)-2,3-diazaspiro[4,4]non-1-en-1-yl)propyl)phenoxy)propanoic acid (Example 24) in place of 2-(4-(3-(1-(4-(tert-butyl) benzyl)-4,4-dimethyl-5-oxo-4,5-dihydro-1H-pyrazol-3-yl) propyl)phenoxy)-2-methylpropanoic acid as the coupling partner. LC-MS: 642 (M+H)$^+$.

Example 26: N-cyclopropyl-2-methyl-2-(4-(3-(4-oxo-3-(4-(trifluoromethyl)phenyl)-2,3-diazaspiro[4,4]non-1-en-1-yl)propyl)phenoxy)propanamide

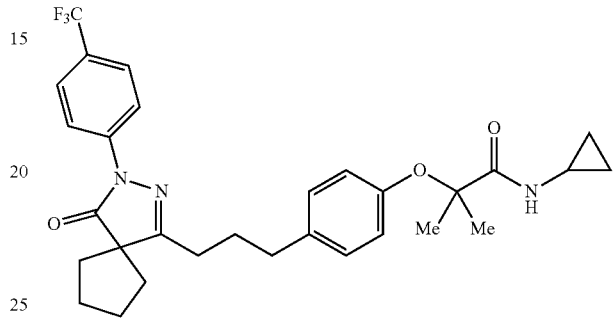

Prepared in an analogous manner to Example 3 but using 2-methyl-2-(4-(3-(4-oxo-3-(4-(trifluoromethyl)phenyl)-2,3-diazaspiro[4,4]non-1-en-1-yl)propyl)phenoxy)propanoic acid (Example 24) in place of 2-(4-(3-(1-(4-(tert-butyl) benzyl)-4,4-dimethyl-5-oxo-4,5-dihydro-1H-pyrazol-3-yl) propyl)phenoxy)-2-methylpropanoic acid, and cyclopropylamine in place of benzyl amine as the coupling partners. LC-MS: 542 (M+H)$^+$.

Example 27: 2-methyl-2-(4-(3-(4-oxo-3-(4-(trifluoromethyl)phenyl)-2,3-diazaspiro[4,4]non-1-en-1-yl) propyl)phenoxy)-N-(2,2,2-trifluoroethyl)propanamide

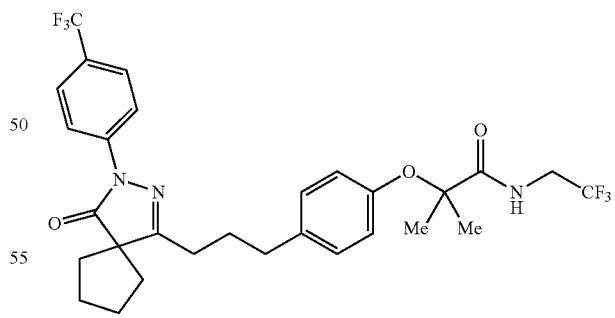

Prepared in an analogous manner to Example 3 but using 2-methyl-2-(4-(3-(4-oxo-3-(4-(trifluoromethyl)phenyl)-2,3-diazaspiro[4,4]non-1-en-1-yl)propyl)phenoxy)propanoic acid (Example 24) in place of 2-(4-(3-(1-(4-(tert-butyl) benzyl)-4,4-dimethyl-5-oxo-4,5-dihydro-1H-pyrazol-3-yl) propyl)phenoxy)-2-methylpropanoic acid, and 2,2,2-trifluoroethylamine in place of benzyl amine as the coupling partners. LC-MS: 584 (M+H)$^+$.

Example 28: 2-methyl-2-(4-(3-(4-oxo-3-(4-(trifluoromethoxy)phenyl)-2,3-diazaspiro[4,4]non-1-en-1-yl)propyl)phenoxy)propanoic acid

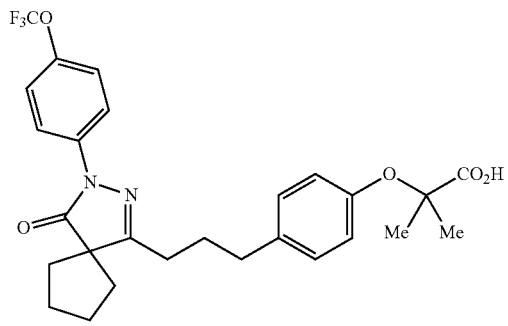 [SMILES: CC(C)(Oc1ccc(CCCC2=NN(c3ccc(OC(F)(F)F)cc3)C(=O)C23CCCC3)cc1)C(=O)O]

Prepared in an analogous manner to Example 10 but using 1-iodo-4-(trifluoromethoxy)benzene in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 519 (M+H)+.

Example 29: N-cyclopropyl-2-methyl-2-(4-(3-(4-oxo-3-(4-(trifluoromethoxy)phenyl)-2,3-diazaspiro[4,4]non-1-en-1-yl)propyl)phenoxy)propanamide

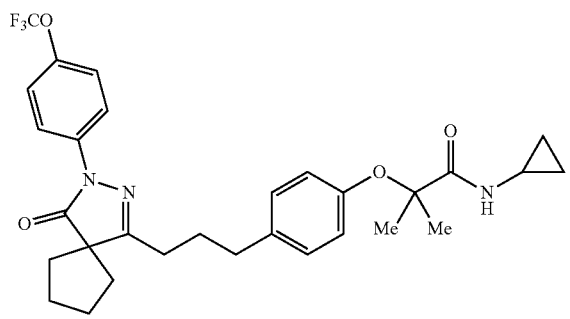 [SMILES: CC(C)(Oc1ccc(CCCC2=NN(c3ccc(OC(F)(F)F)cc3)C(=O)C23CCCC3)cc1)C(=O)NC1CC1]

Prepared in an analogous manner to Example 3 but using 2-methyl-2-(4-(3-(4-oxo-3-(4-(trifluoromethoxy)phenyl)-2,3-diazaspiro[4,4]non-1-en-1-yl)propyl)phenoxy)propanoic acid (Example 28) in place of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid, and cyclopropylamine in place of benzyl amine as the coupling partners. LC-MS: 558 (M+H)+.

Example 30: 2-methyl-2-(4-(3-(4-oxo-3-(4-(trifluoromethoxy)phenyl)-2,3-diazaspiro[4,4]non-1-en-1-yl)propyl)phenoxy)-N-(2,2,2-trifluoroethyl)propanamide

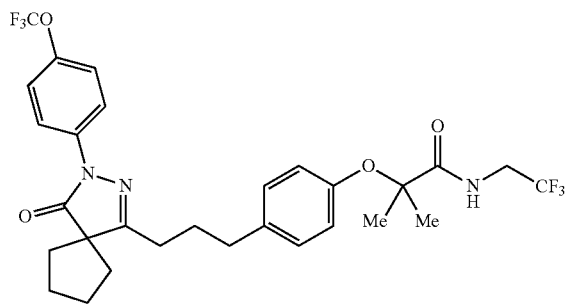 [SMILES: CC(C)(Oc1ccc(CCCC2=NN(c3ccc(OC(F)(F)F)cc3)C(=O)C23CCCC3)cc1)C(=O)NCC(F)(F)F]

Prepared in an analogous manner to Example 3 but using 2-methyl-2-(4-(3-(4-oxo-3-(4-(trifluoromethoxy)phenyl)-2,3-diazaspiro[4,4]non-1-en-1-yl)propyl)phenoxy)propanoic acid (Example 28) in place of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid, and 2,2,2-trifluoroethylamine in place of benzyl amine as the coupling partners. LC-MS: 600 (M+H)+.

Example 31: 2-(4-(3-(3-(3,4-dimethylphenyl)-4-oxo-2,3-diazaspiro[4,4]non-1-en-1-yl)propyl)phenoxy)-2-methylpropanoic acid

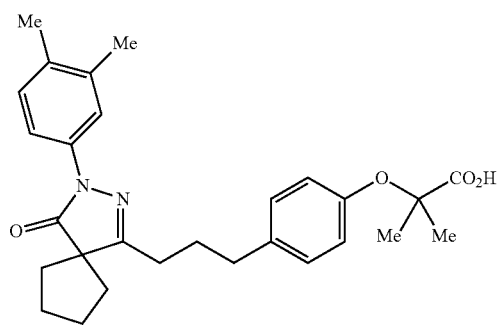 [SMILES: Cc1ccc(N2N=C(CCCc3ccc(OC(C)(C)C(=O)O)cc3)C3(CCCC3)C2=O)cc1C]

Prepared in an analogous manner to Example 10 but using 4-iodo-1,2-dimethylbenzene in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 463 (M+H)+.

Example 32: N-cyclopropyl-2-(4-(3-(3-(3,4-dimethylphenyl)-4-oxo-2,3-diazaspiro[4,4]non-1-en-1-yl)propyl)phenoxy)-2-methylpropanamide

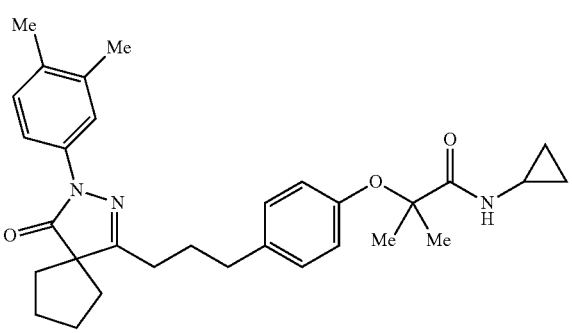 [SMILES: Cc1ccc(N2N=C(CCCc3ccc(OC(C)(C)C(=O)NC4CC4)cc3)C3(CCCC3)C2=O)cc1C]

Prepared in an analogous manner to Example 3 but using 2-(4-(3-(3-(3,4-dimethylphenyl)-4-oxo-2,3-diazaspiro[4,4]non-1-en-1-yl)propyl)phenoxy)-2-methylpropanoic acid (Example 31) in place of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid, and cyclopropylamine in place of benzyl amine as the coupling partners. LC-MS: 502 (M+H)+.

Example 33: 2-(4-(3-(3-(3,4-dimethylphenyl)-4-oxo-2,3-diazaspiro[4,4]non-1-en-1-yl)propyl)phenoxy)-2-methyl-N-(2,2,2-trifluoroethyl)propanamide

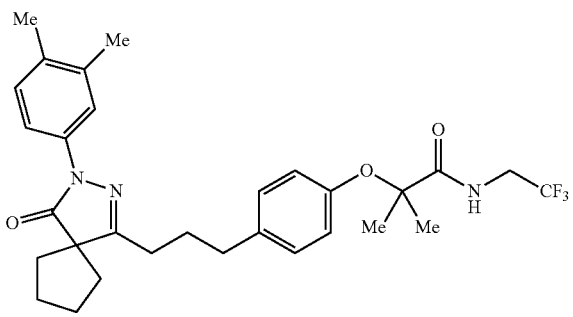 [SMILES: Cc1ccc(N2N=C(CCCc3ccc(OC(C)(C)C(=O)NCC(F)(F)F)cc3)C3(CCCC3)C2=O)cc1C]

Prepared in an analogous manner to Example 3 but using 2-methyl-2-(4-(3-(4-oxo-3-(4-(trifluoromethoxy)phenyl)-2,3-diazaspiro[4,4]non-1-en-1-yl)propyl)phenoxy)propanoic acid (Example 31) in place of 2-(4-(3-(1-(4-(tert-butyl)benzyl)-4,4-dimethyl-5-oxo-4,5-dihydro-1H-pyrazol-3-yl)propyl)phenoxy)-2-methylpropanoic acid, and 2,2,2-trifluoroethylamine in place of benzyl amine as the coupling partners. LC-MS: 544 (M+H)$^+$.

Example 34: 2-methyl-2-(4-(3-(4-oxo-3-(4-(trifluoromethyl)benzyl)-2,3-diazaspiro[4,4]non-1-en-1-yl)propyl)phenoxy)propanoic acid

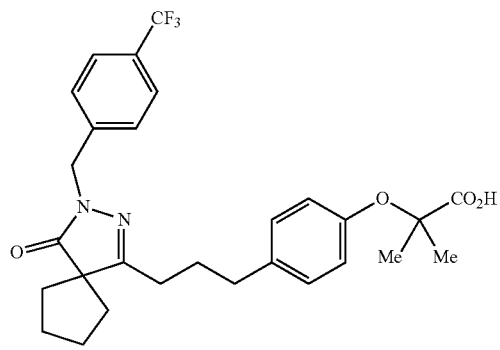 [SMILES: CC(C)(Oc1ccc(CCCC2=NN(Cc3ccc(C(F)(F)F)cc3)C(=O)C23CCCC3)cc1)C(=O)O]

Prepared in an analogous manner to Example 23 but using 4-(trifluoromethyl)benzyl bromide in place of 4-tert-butylbenzyl bromide as the electrophile in step 5. LC-MS: 517 (M+H)$^+$.

Example 35: 2-methyl-2-(4-(3-(4-oxo-3-(3-(trifluoromethyl)phenyl)-2,3-diazaspiro[4,4]non-1-en-1-yl)propyl)phenoxy)propanoic acid

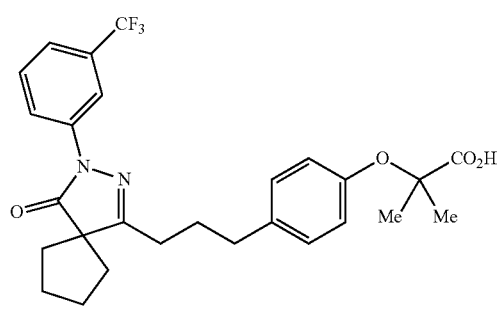

Prepared in an analogous manner to Example 10 but using 3-iodobenzotrifluoride in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 503 (M+H)$^+$.

Example 36: 2-methyl-2-(4-(3-(4-oxo-3-(3-(trifluoromethoxy)phenyl)-2,3-diazaspiro[4,4]non-1-en-1-yl)propyl)phenoxy)propanoic acid

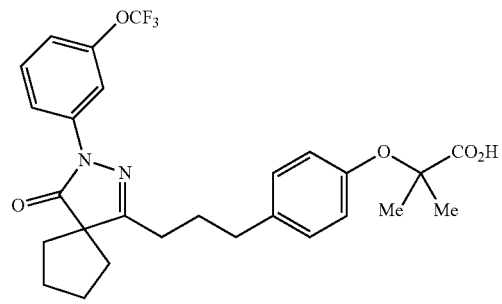 [SMILES: CC(C)(Oc1ccc(CCCC2=NN(c3cccc(OC(F)(F)F)c3)C(=O)C23CCCC3)cc1)C(=O)O]

Prepared in an analogous manner to Example 10 but using 3-(trifluoromethoxy)iodobenzene in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 519 (M+H)$^+$.

Example 37: 2-methyl-2-(4-(3-(3-(naphthalen-2-yl)-4-oxo-2,3-diazaspiro[4,4]non-1-en-1-yl)propyl)phenoxy)propanoic acid

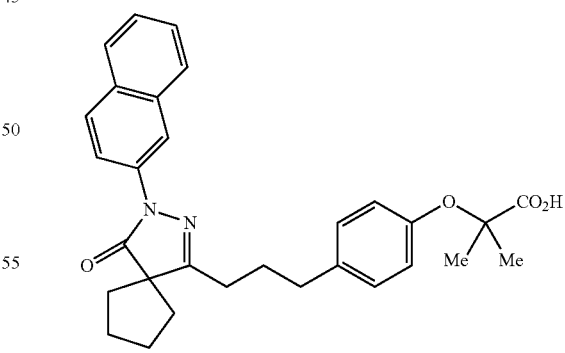

Prepared in an analogous manner to Example 10 but using 2-iodonaphthalene in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 485 (M+H)$^+$.

Example 38: 2-(4-(3-(3-([1,1'-biphenyl]-3-yl)-4-oxo-2,3-diazaspiro[4,4]non-1-en-1-yl)propyl)phenoxy)-2-methylpropanoic acid

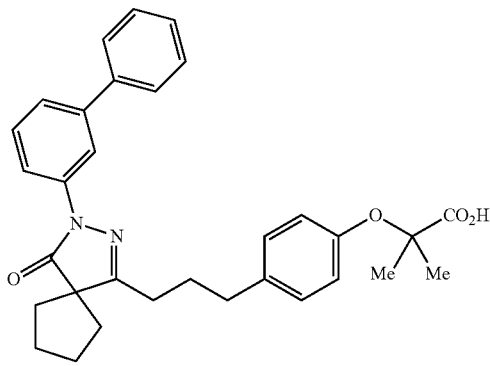 [SMILES: CC(C)(Oc1ccc(CCCC2=NN(c3cccc(-c4ccccc4)c3)C(=O)C23CCCC3)cc1)C(=O)O]

Prepared in an analogous manner to Example 10 but using 3-iodobiphenyl in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 511 (M+H)$^+$.

Example 39: 2-methyl-2-(4-(3-(3-(4-methyl-3-(trifluoromethyl)phenyl)-4-oxo-2,3-diazaspiro[4,4]non-1-en-1-yl)propyl)phenoxy)propanoic acid

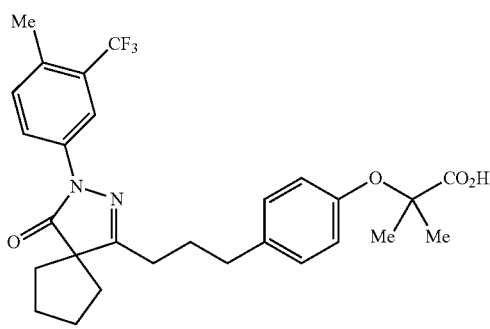 [SMILES: Cc1ccc(N2N=C(CCCc3ccc(OC(C)(C)C(=O)O)cc3)C3(CCCC3)C2=O)cc1C(F)(F)F]

Prepared in an analogous manner to Example 10 but using 5-iodo-2-methylbenzotrifluoride in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 517 (M+H)$^+$.

Example 40: 2-(4-(3-(3-(3-(tert-butyl)phenyl)-4-oxo-2,3-diazaspiro[4,4]non-1-en-1-yl)propyl)phenoxy)-2-methylpropanoic acid

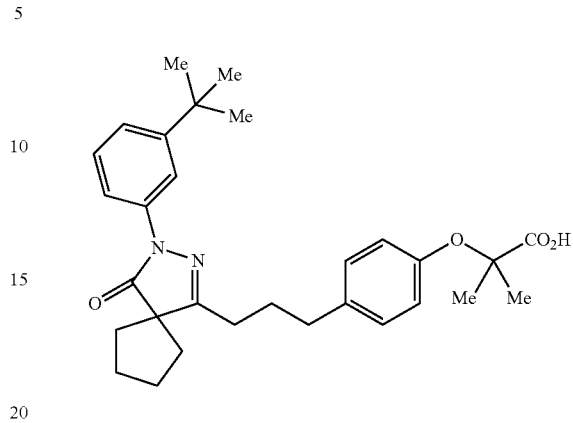

Prepared in an analogous manner to Example 10 but using 1-(tert-butyl)-3-iodobenzene in place of iodobenzene, and ethyl 2-methyl-2-(4-(3-(4-oxo-2,3-diazaspiro[4,4]non-1-en-1-yl)propyl)phenoxy)propanoate (Example 23, Step 4) in place of ethyl 2-(4-(3-(4,4-dimethyl-5-oxo-4,5-dihydro-1H-pyrazol-3-yl)propyl)phenoxy)-2-methylpropanoate as coupling partners in step 1. LC-MS: 491 (M+H)$^+$.

Example 41: 2-methyl-2-(4-(3-(5-oxo-4,4-dipropyl-1-(4-(trifluoromethyl)phenyl)-4,5-dihydro-1H-pyrazol-3-yl)propyl)phenoxy)propanoic acid

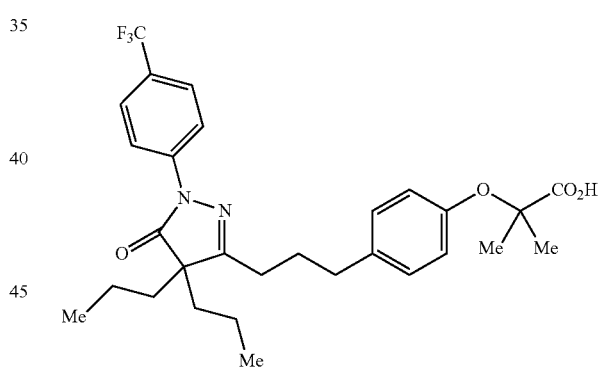

Step 1: To an ethanol solution (0.2 M) of methyl 2,2-diallyl-6-(4-((1-ethoxy-2-methyl-1-oxopropan-2-yl)oxy)phenyl)-3-oxohexanoate (1 eq., Example 23, Step 1) was added palladium black (0.1 eq., 10% w/w (wet) over carbon). The resulting suspension was evacuated and backfilled with hydrogen gas (3×). Then, the reaction mixture was stirred under a static hydrogen atmosphere maintained with a balloon for 16 h. The mixture was carefully quenched with DCM and filtered through a bed of DCM-wetted celite. The insolubles were then washed further with DCM. Concentration of the filtrate thus obtained in vacuo furnished the desired compound as a colorless oil (93% yield).

Step 2: To an ethanol solution (0.18 M) of methyl 6-(4-((1-ethoxy-2-methyl-1-oxopropan-2-yl)oxy)phenyl)-3-oxo-2,2-dipropylhexanoate (1 eq.) from the previous step was added hydrazine monohydrate (1.5 eq.). The reaction vessel was then tightly sealed and heated at 120° C. behind a blast shield for 96 h. After cooling to RT, the volatiles were then removed in vacuo and the resulting residue was partitioned between ether and 10% aq. HCl. The aqueous layer was separated and back-extracted with ether. The combined organic extracts were then washed further with water and brine, dried over $Na_2SO_4$, filtered and the filtrate concentrated in vacuo. Purification of the crude product thus obtained by way of column chromatography ($SiO_2$, gradient elution, Hex→1:1 (v/v) Hex: EtOAc) afforded the desired product as a colorless oil (5% yield).

Step 3: To a DMSO solution (0.03 M) of ethyl 2-methyl-2-(4-(3-(5-oxo-4,4-dipropyl-4,5-dihydro-1H-pyrazol-3-yl)propyl)phenoxy)propanoate (1 eq.) from the previous step was added 4-iodobenzotrifluoride (1.5 eq.), copper(I) iodide (0.1 eq.), L-proline (0.2 eq.) and potassium carbonate (3 eq.). The resulting suspension was then deoxygenated via sub-surface purging with a stream of nitrogen for 15 min. Then, the reaction vessel was tightly sealed and the reaction mixture was heated at 100° C. for 16 h. After cooling the reaction suspension to RT, the reaction was carefully quenched with 10% aq. HCl and extracted with ether. The combined organic extracts were then washed further with water and brine, dried over $Na_2SO_4$, filtered and the filtrate concentrated in vacuo. Purification of the crude product thus obtained by way of column chromatography ($SiO_2$, gradient elution, 9:1→1:1 (v/v) Hex: EtOAc) afforded the desired product as a pale yellow oil (36% yield).

Step 4: To a 2:1 (v/v) THF: MeOH solution (0.1 M) of ethyl 2-methyl-2-(4-(3-(5-oxo-4,4-dipropyl-1-(4-(trifluoromethyl)phenyl)-4,5-dihydro-1H-pyrazol-3-yl)propyl)phenoxy)propanoate (1 eq.) from the previous step was added lithium hydroxide (3 eq., 2 N aq. solution). The resulting biphasic mixture was then stirred at RT for 16 h. The volatiles were then removed in vacuo and the resulting residue was acidified with 1 N aq. HCl to pH of ~3. The aqueous suspension thus obtained was then extracted with ether. The combined organic extracts were then washed further with water and brine, dried over $Na_2SO_4$ and filtered. Concentration of the filtrate in vacuo afforded the title compound as a viscous oil (76% yield). LC-MS: 533 $(M+H)^+$.

Example 42: 2-methyl-2-(4-(3-(5-oxo-4,4-dipropyl-1-(3-(trifluoromethyl)phenyl)-4,5-dihydro-1H-pyrazol-3-yl)propyl)phenoxy)propanoic acid

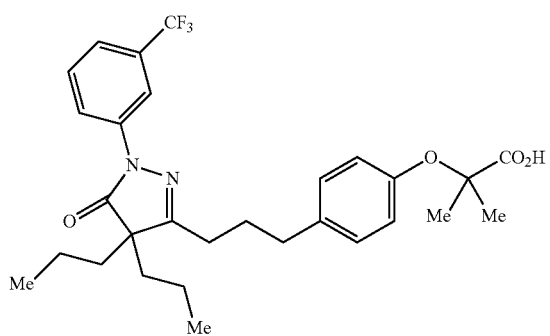 [SMILES: CCCC1(CCC)C(=O)N(c2cccc(C(F)(F)F)c2)N=C1CCCc1ccc(OC(C)(C)C(=O)O)cc1]

Prepared in an analogous manner to Example 41 but using 3-iodobenzotrifluoride in place of 4-iodobenzotrifluoride as the aryl iodide coupling partner in step 3. LC-MS: 533 $(M+H)^+$.

Example 43: 4,4-dimethyl-3-(3-(4-((4,4,4-trifluoro-3-hydroxy-2-methylbutan-2-yl)oxy)phenyl)propyl)-1-(4-(trifluoromethyl)phenyl)-1H-pyrazol-5(4H)-one

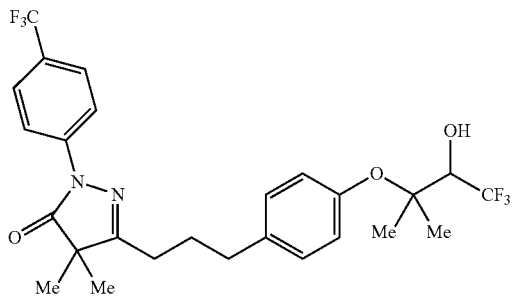 [SMILES: CC1(C)C(=O)N(c2ccc(C(F)(F)F)cc2)N=C1CCCc1ccc(OC(C)(C)C(O)C(F)(F)F)cc1]

Step 1: To a THF solution (0.23 M) of 2-(4-(3-(4,4-dimethyl-5-oxo-1-(4-(trifluoromethyl)phenyl)-4,5-dihydro-1H-pyrazol-3-yl)propyl)phenoxy)-2-methylpropanoic acid (1 eq., Example 19) was added sequentially at 0° C. Hunig's base (1.5 eq.) and ethyl chloroformate (1.2 eq.). The resulting mixture was then allowed to warm slowly to RT over 16 h. The now white suspension was quenched with methanol (30 eq.) and then added sodium borohydride (6 eq.) portionwise over a period of 5 min. After another 5 h of stirring at RT, the reaction mixture was diluted with 10% aq. HCl and extracted with ether. The combined organic extracts were washed further with 1 N aq. NaOH, water and brine, dried over $Na_2SO_4$, filtered and the filtrate concentrated in vacuo. Purification of the crude product thus obtained by way of column chromatography ($SiO_2$, gradient elution, Hex→1:1 (v/v) Hex: EtOAc) afforded the desired product as a viscous oil (90% yield).

Step 2. To a DCM solution (0.08 M) of 3-(3-(4-((1-hydroxy-2-methylpropan-2-yl)oxy)phenyl)propyl)-4,4-dimethyl-1-(4-(trifluoromethyl)phenyl)-1H-pyrazol-5(4H)-one (1 eq.) from the previous step was added sequentially at 0° C. sodium bicarbonate (1.5 eq.) and Dess-Martin periodinane (1.5 eq.). The resulting suspension was then allowed to warm slowly to RT over 3 h before it was diluted with ether and quenched with 5% aq. $Na_2S_2O_3$. The organic layer was separated, washed further with 1 N aq. NaOH, water and brine, dried over $Na_2SO_4$ and filtered. Concentration of the filtrate in vacuo funished the desired product as a viscous oil which was used immediately without further purification.

Step 3: To a THF solution (0.04 M) of 2-(4-(3-(4,4-dimethyl-5-oxo-1-(4-(trifluoromethyl)phenyl)-4,5-dihydro-1H-pyrazol-3-yl)propyl)phenoxy)-2-methylpropanal (1 eq.) from the previous step was added sequentially trimethyl (trifluoromethyl)silane (4 eq.) and TBAF (0.2 eq., 1.0 M in THF). The resulting golden yellow solution was then allowed to stir at RT for 16 h before another 1.5 eq. of TBAF was added. After another 30 min of stirring at RT, the reaction mixture was diluted with ether and washed sequentially with 10% aq. HCl, water and brine. The organic extract was then dried over $Na_2SO_4$, filtered and the filtrate concentrated in vacuo. Purification of the crude product thus obtained by way of column chromatography ($SiO_2$, gradient elution, Hex→4:1 (v/v) Hex: acetone) afforded the title compound as a pale yellow oil (68% yield over 2 steps). LC-MS: 531 $(M+H)^+$.

Example 44: 4,4-dimethyl-3-(3-(4-((4,4,4-trifluoro-2-methyl-3-oxobutan-2-yl)oxy)phenyl)propyl)-1-(4-(trifluoromethyl)phenyl)-1H-pyrazol-5(4H)-one

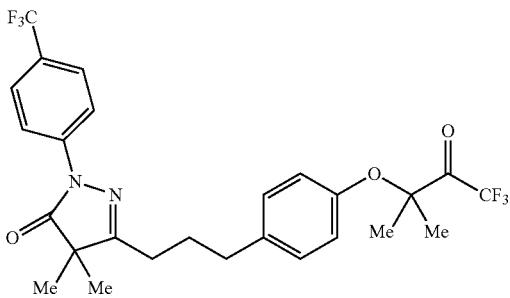 [SMILES: CC(C)(Oc1ccc(CCCC2=NN(c3ccc(C(F)(F)F)cc3)C(=O)C2(C)C)cc1)C(=O)C(F)(F)F]

To a DCM solution (0.01 M) of 4,4-dimethyl-3-(3-(4-((4,4,4-trifluoro-3-hydroxy-2-methylbutan-2-yl)oxy)phenyl)propyl)-1-(4-(trifluoromethyl)phenyl)-1H-pyrazol-5(4H)-one (1 eq., Example 43) was added sequentially at 0° C. sodium bicarbonate (1.5 eq.) and Dess-Martin periodinane (4.5 eq.). The resulting suspension was then allowed to warm slowly to RT over 16 h before it was diluted with ether and quenched with 5% aq. Na$_2$S$_2$O$_3$. The organic layer was separated, washed further with 1 N aq. NaOH, water and brine, dried over Na$_2$SO$_4$, filtered and the filtrate concentrated in vacuo. Purification of the crude product thus obtained by way of column chromatography (SiO$_2$, gradient elution, Hex→1:1 (v/v) Hex: EtOAc) afforded the title compound as a mixture of the ketone (major) and the corresponding hydrate (minor). LC-MS: 529 (M+H)$^+$.

Example 45: 4-(3-(4-((1-amino-2-methylpropan-2-yl)oxy)phenyl)propyl)-2-(4-(trifluoromethyl)phenyl)-2,3-diazaspiro[4,4]non-3-en-1-one

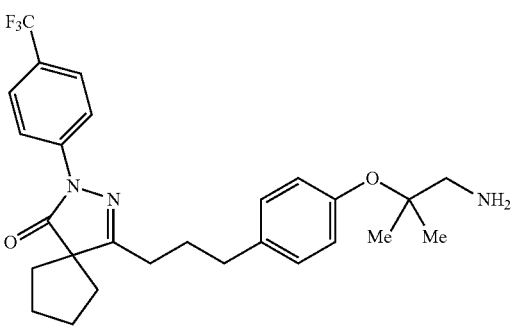 [SMILES: CC(C)(CN)Oc1ccc(CCCC2=NN(c3ccc(C(F)(F)F)cc3)C(=O)C23CCCC3)cc1]

Step 1: To a THF solution (0.13 M) of 2-methyl-2-(4-(3-(4-oxo-3-(4-(trifluoromethyl)phenyl)-2,3-diazaspiro[4,4]non-1-en-1-yl)propyl)phenoxy)propanoic acid (1 eq., Example 24) was added sequentially at 0° C. triethylamine (1.5 eq.) and ethyl chloroformate (1.2 eq.). The resulting mixture was then allowed to warm slowly to RT over 16 h. The now pale yellow suspension was quenched with methanol (30 eq.) and then added sodium borohydride (6 eq.) portionwise over a period of 5 min. After another 8 h of stirring at RT, the reaction mixture was diluted with 10% aq. HCl and extracted with ether. The combined organic extracts were washed further with 1 N aq. NaOH, water and brine, dried over Na$_2$SO$_4$, filtered and the filtrate concentrated in vacuo. Purification of the crude product thus obtained by way of column chromatography (SiO$_2$, gradient elution, 9:1 (v/v) Hex: EtOAc→EtOAc) afforded the desired product as a white foam (78% yield).

Step 2: To a DCM solution (0.04 M) of 4-(3-(4-((1-hydroxy-2-methylpropan-2-yl)oxy)phenyl)propyl)-2-(4-(trifluoromethyl)phenyl)-2,3-diazaspiro[4,4]non-3-en-1-one (1 eq.) from the previous step was added sequentially at 0° C. triethylamine (1.5 eq.) and methanesulfonyl chloride (1.5 eq.). The resulting suspension was then allowed to warm slowly to RT over 16 h before it was diluted with ether and washed sequentially with cold water, cold 10% aq. HCl and cold brine. The organic layer was then dried over Na$_2$SO$_4$ and filtered. Concentration of the filtrate in vacuo funished the desired product as a pale yellow oil which was used immediately without further purification.

Step 3: To a DMSO solution (0.01 M) of 2-methyl-2-(4-(3-(4-oxo-3-(4-(trifluoromethyl)phenyl)-2,3-diazaspiro[4,4]non-1-en-1-yl)propyl)phenoxy)propyl methanesulfonate (1 eq.) from the previous step was added sodium azide (10 eq.). The reaction vessel was then tightly sealed and heated at 140° C. for 16 h behind a blast shield. The resulting dark brown suspension was diluted with ether and washed sequentially with water, 10% aq. HCl, water and brine. The organic extract was then dried over Na$_2$SO$_4$, filtered and the filtrate concentrated in vacuo. Purification of the crude product thus obtained by way of column chromatography (SiO$_2$, gradient elution, Hex→1:1 (v/v) Hex: EtOAc) afforded the title compound as a pale yellow oil (91% yield over 2 steps).

Step 4: To an ethanol solution (0.01 M) of 4-(3-(4-((1-azido-2-methylpropan-2-yl)oxy)phenyl)propyl)-2-(4-(trifluoromethyl)phenyl)-2,3-diazaspiro[4,4]non-3-en-1-one (1 eq.) from the previous step was added palladium black (0.1 eq., 10% w/w (wet) over carbon). The resulting suspension was evacuated and back-filled with hydrogen gas (3×). Then, the reaction mixture was stirred under a static hydrogen atmosphere maintained with a balloon for 3 h. The mixture was carefully quenched with DCM and filtered through a bed of DCM-wetted celite. The insolubles were then washed further with DCM. Concentration of the filtrate thus obtained in vacuo furnished the title compound as a colorless oil (85% yield). LC-MS: 488 (M+H)$^+$.

Example 46: N-(2-methyl-2-(4-(3-(4-oxo-3-(4-(trifluoromethyl)phenyl)-2,3-diazaspiro[4,4]non-1-en-1-yl)propyl)phenoxy)propyl)benzenesulfonamide

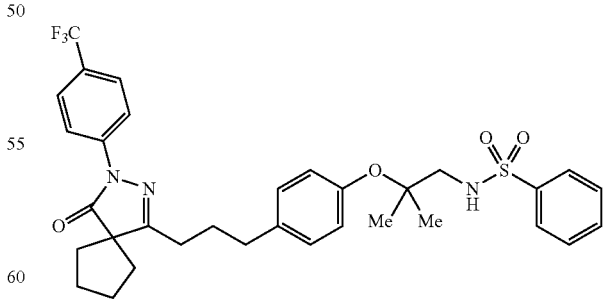

To a DCM solution (0.006 M) of 4-(3-(4-((1-amino-2-methylpropan-2-yl)oxy)phenyl)propyl)-2-(4-(trifluoromethyl)phenyl)-2,3-diazaspiro[4,4]non-3-en-1-one (1 eq., Example 45) was added sequentially triethylamine (1 eq.) and benzenesulfonyl chloride (1.1 eq.). After 16 h of stirring at RT, the volatiles were then removed in vacuo and the resulting residue was directly subjected to preparative HPLC (gradient elution: 7:3 (v/v) H₂O: MeCN+0.1% TFA→MeCN+0.1% TFA). The title compound was obtained as a white foam. LC-MS: 628 (M+H)⁺.

Example 47: N-(2-methyl-2-(4-(3-(4-oxo-3-(4-(trifluoromethyl)phenyl)-2,3-diazaspiro[4,4]non-1-en-1-yl)propyl)phenoxy)propyl)benzamide

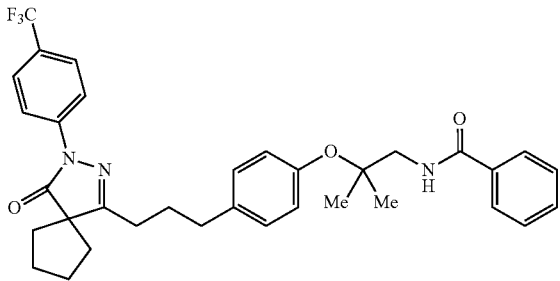 [SMILES: CC(C)(CNC(=O)c1ccccc1)Oc1ccc(CCCC2=NN(c3ccc(C(F)(F)F)cc3)C(=O)C23CCCC3)cc1]

Prepared in an analogous manner to Example 46 but using benzoyl chloride in place of benzenesulfonyl chloride as the electrophile. LC-MS: 592 (M+H)⁺.

Example 48: 2-(4-(3-(4,4-dimethyl-5-oxo-1-(4-(trifluoromethyl)phenyl)-4,5-dihydro-1H-pyrazol-3-yl)propyl)phenoxy)-2-phenylacetic acid

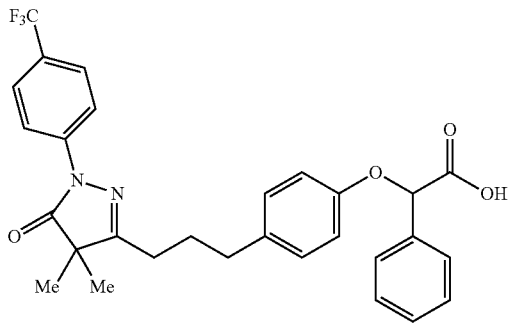 [SMILES: CC1(C)C(=O)N(c2ccc(C(F)(F)F)cc2)N=C1CCCc1ccc(OC(C(=O)O)c2ccccc2)cc1]

Step 1: To an acetonitrile solution (0.05 M) of 4-(4-methoxyphenyl)butanoic acid (1 eq.) was added CDI (1.1 eq.). The resulting yellow solution was then allowed to stir at RT for 2.5 h before it was added dropwise, over a period of 1.5 h, into a white suspension of potassium 3-methoxy-3-oxopropanoate (2.1 eq.), magnesium chloride (2.5 eq.) and triethylamine (3.2 eq.). The resulting suspension was then stirred at RT for 16 h and finally heated at reflux for another 96 h. The crude reaction suspension thus obtained was cooled to RT and diluted with EtOAc. The insolubles were then removed via filtration and rinsed further with EtOAc and DCM. The filtrate thus obtained was concentrated in vacuo, re-taken up in EtOAc and washed sequentially with 10% aq. HCl, water and brine. The organic extract was then dried over Na₂SO₄ and filtered. Concentration of the filtrate in vacuo afford the desired product as an orange oil which can be used without further purification.

Step 2: To a DMSO solution (0.2 M) of methyl 6-(4-methoxyphenyl)-3-oxohexanoate (1 eq.) from the previous step was added cesium carbonate (3 eq.) and iodomethane (3 eq.). The resulting mixture was then allowed to stir at RT for 16 h. The crude reaction mixture thus obtained was diluted with ether and washed sequentially with cold water, 10% aq. HCl, 1 N aq. NaOH, water and finally brine. The organic extract was then dried over Na₂SO₄, and filtered. Concentration of the filtrate in vacuo afforded the desired product as a golden yellow oil which can be used without further purification.

Step 3: To an ethanol solution (0.75 M) of methyl 6-(4-methoxyphenyl)-2,2-dimethyl-3-oxohexanoate (1 eq.) from the previous step was added hydrazine monohydrate (4 eq.). The reaction vessel was then tightly sealed and heated at 80° C. behind a blast shield for 48 h. After cooling to RT, the volatiles were then removed in vacuo and the resulting residue was partitioned between ether and 10% aq. HCl. The aqueous layer was separated and back-extracted with ether. The combined organic extracts were then washed further with water and brine, dried over Na₂SO₄ and filtered. Concentration of the filtrate in vacuo afforded the desired product as a golden yellow oil which can be used without further purification.

Step 4: To a DMSO solution (0.13 M) of 3-(3-(4-methoxyphenyl)propyl)-4,4-dimethyl-1H-pyrazol-5(4H)-one (1 eq.) from the previous step was added 4-iodobenzotrifluoride (1.5 eq.), copper(I) iodide (0.1 eq.), L-proline (0.2 eq.) and potassium carbonate (3 eq.). The resulting suspension was then deoxygenated via sub-surface purging with a stream of nitrogen for 15 min. Then, the reaction vessel was tightly sealed and the reaction mixture was heated at 95° C. for 16 h. After cooling the reaction suspension to RT, the reaction was carefully quenched with 10% aq. HCl and extracted with ether. The combined organic extracts were then washed further with water and brine, dried over Na₂SO₄, filtered and the filtrate concentrated in vacuo. Purification of the crude product thus obtained by way of column chromatography (SiO₂, gradient elution, 9:1→1:1 (v/v) Hex: EtOAc) afforded the desired product as a pale yellow oil that solidified upon standing (74% yield over 4 steps).

Step 5: To a DCM solution (0.07 M) of 3-(3-(4-methoxyphenyl)propyl)-4,4-dimethyl-1-(4-(trifluoromethyl)phenyl)-1H-pyrazol-5(4H)-one (1 eq.) from the previous step was added at −78° C. boron tribromide (3 eq., 1 M in DCM) dropwise over a period of 5 min. The resulting solution was then warmed slowly to RT over 16 h before the reaction was quenched, at −78° C., with the dropwise addition of methanol. The reaction mixture was then diluted with EtOAc and washed sequentially with 10% aq. HCl, water and brine. The organic extract was dried over Na₂SO₄, filtered and the filtrate concentrated in vacuo. Purification of the crude product thus obtained by way of column chromatography (SiO₂, gradient elution, 4:1 (v/v) Hex: EtOAc→EtOAc) afforded the desired product as a pale yellow oil that solidified upon standing (98% yield).

Step 6: To a DMSO solution (0.07 M) of 3-(3-(4-hydoxyphenyl)propyl)-4,4-dimethyl-1-(4-(trifluoromethyl)phenyl)-1H-pyrazol-5(4H)-one (1 eq.) from the previous step was added cesium carbonate (1.5 eq.) and ethyl 2-bromo-2-phenylacetate (1.2 eq.). The resulting mixture was then stirred at RT for 3 h before the reaction was quenched with the addition of 10% aq. HCl and ether. The organic layer was separated and washed further with water and brine, dried over Na₂SO₄, filtered and the filtrate concentrated in vacuo. Purification of the crude product thus obtained by way of column chromatography (SiO$_2$, gradient elution, 9:1→3:7 (v/v) Hex: EtOAc) afforded the desired product as a colorless oil (89% yield).

Step 7: To a 2:1 (v/v) THF: MeOH solution (0.024 M) of ethyl 2-(4-(3-(4,4-dimethyl-5-oxo-1-(4-(trifluoromethyl)phenyl)-4,5-dihydro-1H-pyrazol-3-yl)propyl)phenoxy)-2-phenylacetate (1 eq.) from the previous step was added lithium hydroxide (3 eq., 2 N aq. solution). The resulting biphasic mixture was then stirred at RT for 1.5 h. The volatiles were then removed in vacuo and the resulting residue was acidified with 1 N aq. HCl to pH of ~3. The aqueous suspension thus obtained was then extracted with EtOAc. The combined organic extracts were then washed further with water and brine, dried over Na$_2$SO$_4$, and filtered. Concentration of the filtrate in vacuo. afforded the title compound as a white solid (95% yield). LC-MS: 525 (M+H)$^+$.

Example 49: 2-(4-(3-(4,4-dimethyl-5-oxo-1-(4-(trifluoromethyl)phenyl)-4,5-dihydro-1H-pyrazol-3-yl)propyl)phenoxy)acetic acid

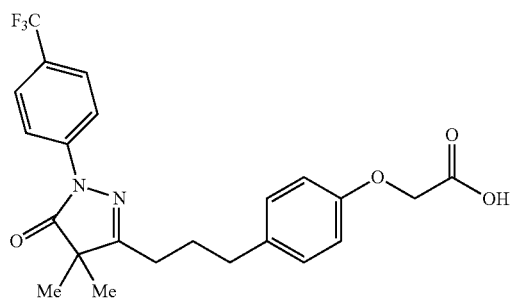 [SMILES: CC1(C)C(=O)N(c2ccc(C(F)(F)F)cc2)N=C1CCCc1ccc(OCC(=O)O)cc1]

Prepared in an analogous manner to Example 48 but using ethyl 2-bromoacetate in place of ethyl 2-bromo-2-phenylacetate as the electrophile in step 6. LC-MS: 449 (M+H)$^+$.

Example 50: 1-(4-(3-(4,4-dimethyl-5-oxo-1-(4-(trifluoromethyl)phenyl)-4,5-dihydro-1H-pyrazol-3-yl)propyl)phenoxy)cyclobutanecarboxylic acid

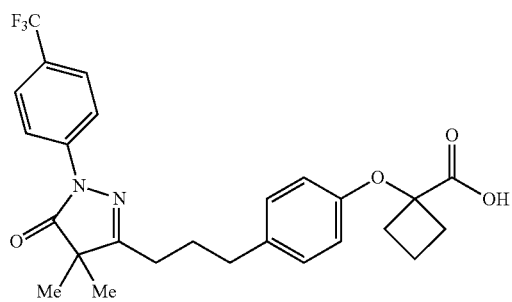 [SMILES: CC1(C)C(=O)N(c2ccc(C(F)(F)F)cc2)N=C1CCCc1ccc(OC2(C(=O)O)CCC2)cc1]

Prepared in an analogous manner to Example 48 but using ethyl 1-bromocyclobutanecarboxylate in place of ethyl 2-bromo-2-phenylacetate as the electrophile, 100° C. as the reaction temperature and 40 h as the reaction time in step 6. LC-MS: 489 (M+H)$^+$.

Example 51: 1-(4-(3-(4,4-dimethyl-5-oxo-1-(3-(trifluoromethyl)phenyl)-4,5-dihydro-1H-pyrazol-3-yl)propyl)phenoxy)cyclobutanecarboxylic acid

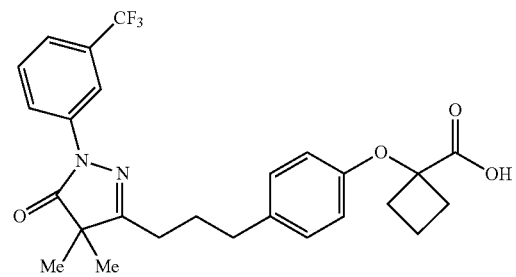 [SMILES: CC1(C)C(=O)N(c2cccc(C(F)(F)F)c2)N=C1CCCc1ccc(OC2(C(=O)O)CCC2)cc1]

Prepared in an analogous manner to Example 48 but using 3-iodobenzotrifluoride in place of 4-iodobenzotrifluoride in step 4. Furthermore in step 6, ethyl 1-bromocyclobutanecarboxylate was used in place of ethyl 2-bromo-2-phenylacetate as the electrophile, 120° C. was the optimal reaction temperature and the alkylation was carried out over 24 h. LC-MS: 489 (M+H)$^+$.

Example 52: 1-(4-(3-(4,4-dimethyl-5-oxo-1-(4-(trifluoromethyl)phenyl)-4,5-dihydro-1H-pyrazol-3-yl)propyl)phenoxy)cyclopentanecarboxylic acid

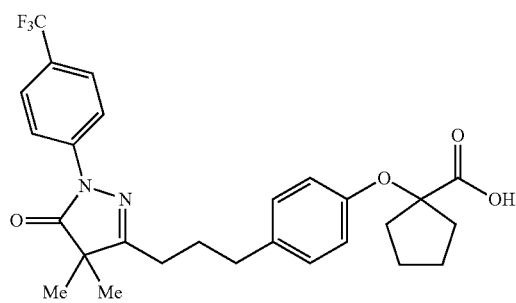 [SMILES: CC1(C)C(=O)N(c2ccc(C(F)(F)F)cc2)N=C1CCCc1ccc(OC2(C(=O)O)CCCC2)cc1]

Prepared in an analogous manner to Example 48 but using ethyl 1-bromocyclopentanecarboxylate in place of ethyl 2-bromo-2-phenylacetate as the electrophile, 120° C. as the reaction temperature and 56 h as the reaction time in step 6. LC-MS: 503 (M+H)$^+$.

Example 53: 2-(4-(3-(4,4-dimethyl-5-oxo-1-(4-(trifluoromethyl)phenyl)-4,5-dihydro-1H-pyrazol-3-yl)propyl)phenoxy)-2-phenylpropanoic acid

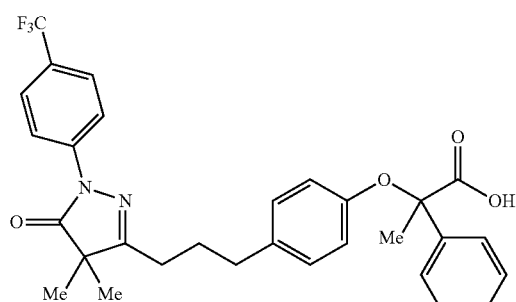

Step 1: To a THF solution (0.05 M) of methyl 2-(4-(3-(4,4-dimethyl-5-oxo-1-(4-(trifluoromethyl)phenyl)-4,5-dihydro-1H-pyrazol-3-yl)propyl)phenoxy)-2-phenylacetate (I eq., Example 48, Step 6) was added dropwise KHMDS (1.5 eq., 1 M THF solution) at −78° C. over a period of 5 min. The resulting pink solution was allowed to stir at −78° C. for another 20 min before iodomethane (1.5 eq.) was added neat, dropwise over a period of 2 min. The reaction mixture was then allowed to warm slowly to RT over 16 h. The crude reaction mixture was then diluted with ether washed sequentially with 10% aq. HCl, water and brine. The organic extract was then dried over Na$_2$SO$_4$, filtered and the filtrate concentrated in vacuo. Purification of the crude product thus obtained by way of column chromatography (SiO$_2$, gradient elution, 9:1→3:7 (v/v) Hex: EtOAc) afforded the racemic product as a pale colorless oil (89% yield). The enantiomers were then be separated on a chiral HPLC (ChiralPak AD column from Daicel Chemical Industries: ID# AD00CJ-DK005, isocratic elution, 1:1 (v/v) EtOH: Hexanes, 25 min run). Retention time of Enantiomer 1: 12.2 min. Retention time of Enantiomer 2: 14.7 min.

Step 2: To a 2:1 (v/v) THF: MeOH solution (0.019 M) of methyl 2-(4-(3-(4,4-dimethyl-5-oxo-1-(4-(trifluoromethyl)phenyl)-4,5-dihydro-1H-pyrazol-3-yl)propyl)phenoxy)-2-phenylpropanoate (I eq.) from the previous step was added lithium hydroxide (3 eq., 2 N aq. solution). The resulting biphasic mixture was then stirred at RT for 1.5 h. The volatiles were then removed in vacuo and the resulting residue was acidified with 1 N aq. HCl to pH of ~3. The aqueous suspension thus obtained was then extracted with EtOAc. The combined organic extracts were then washed further with water and brine, dried over Na$_2$SO$_4$, and filtered. Concentration of the filtrate in vacuo. afforded the title compound as a white solid (Enantiomer 1: 96% yield; Enantiomer 2: 93% yield). LC-MS: 539 (M+H)$^+$.

Example 54: 2-(4-(3-(4,4-dimethyl-5-oxo-1-(3-(trifluoromethyl)phenyl)-4,5-dihydro-1H-pyrazol-3-yl)propyl)phenoxy)-2-phenylpropanoic acid

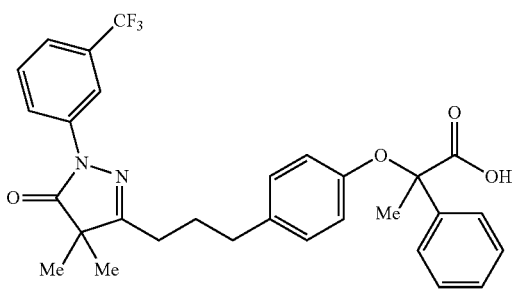 [SMILES: CC1(C)C(=O)N(c2cccc(C(F)(F)F)c2)N=C1CCCc1ccc(OC(C)(C(=O)O)c2ccccc2)cc1]

Prepared in an analogous manner to Example 44 but using ethyl 2-(4-(3-(4,4-dimethyl-5-oxo-1-(3-(trifluoromethyl)phenyl)-4,5-dihydro-1H-pyrazol-3-yl)propyl)phenoxy)-2-phenylacetate in place of methyl 2-(4-(3-(4,4-dimethyl-5-oxo-1-(4-(trifluoromethyl)phenyl)-4,5-dihydro-1H-pyrazol-3-yl)propyl)phenoxy)-2-phenylacetate as the substrate in step 1. Furthermore, the chiral separation was carried out using a modified protocol (ChiralPak AD column from Daicel Chemical Industries: ID# AD00CJ-DK005, isocratic elution, 35:65 (v/v) EtOH: Hexanes, 15 min run). Retention time of Enantiomer 1: 7.2 min. Retention time of Enantiomer 2: 10.7 min. LC-MS: 539 (M+H)$^+$.

Example 55: 2-(4'-(3-(1-(4-(tert-butyl)benzyl)-4,4-dimethyl-5-oxo-4,5-dihydro-1H-pyrazol-3-yl)propyl)-4-ethoxy-[1,1'-biphenyl]-3-yl)acetic acid

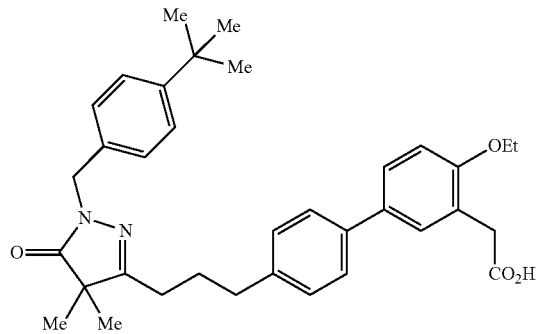 [SMILES: CCOc1ccc(-c2ccc(CCCC3=NN(Cc4ccc(C(C)(C)C)cc4)C(=O)C3(C)C)cc2)cc1CC(=O)O]

Step 1: To an acetonitrile solution (0.14 M) of 4-(4-bromophenyl)butanoic acid (1 eq.) was added CDI (1.1 eq.). The resulting yellow solution was then allowed to stir at RT for 2.5 h before it was added dropwise, over a period of 1.5 h, into a white suspension of potassium 3-methoxy-3-oxopropanoate (2.1 eq.), magnesium chloride (2.5 eq.) and triethylamine (3.2 eq.). The resulting suspension was then stirred at RT for 16 h and finally heated at reflux for another 8 h. The crude reaction suspension thus obtained was cooled to RT and filtered. The filtrate was then concentrated in vacuo and the resulting residue was partitioned between DCM and 20% aq. citric acid. The organic layer was separated and washed further with water and brine, dried over Na$_2$SO$_4$ and filtered. Concentration of the filtrate in vacuo afford the desired product as a white solid (33% yield) which can be used without further purification.

Step 2: To a DMSO solution (0.12 M) of methyl 6-(4-bromophenyl)-3-oxohexanoate (1 eq.) from the previous step was added cesium carbonate (3 eq.) and iodomethane (3 eq.). The resulting mixture was then allowed to stir at RT for 16 h. The crude reaction mixture thus obtained was diluted with ether and washed sequentially with cold water, 10% aq. HCl, 1 N aq. NaOH, water and finally brine. The organic extract was then dried over Na$_2$SO$_4$, filtered and the filtrate concentrated in vacuo. Purification of the crude product thus obtained by way of column chromatography (SiO$_2$, gradient elution, Hex—3:2 (v/v) Hex: EtOAc) afforded the desired product as a colorless oil (92% yield).

Step 3: To an ethanol solution (0.2 M) of methyl 6-(4-bromophenyl)-2,2-dimethyl-3-oxohexanoate (1 eq.) from the previous step was added hydrazine monohydrate (8 eq.). The reaction vessel was then tightly sealed and heated at 50° C. behind a blast shield for 16 h. After cooling to RT, the volatiles were then removed in vacuo and the resulting residue was partitioned between ether and 10% aq. HCl. The aqueous layer was separated and back-extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, isocratic elution, 3:1 (v/v) Hex: acetone) afforded the desired product as a golden yellow oil (92% yield).

Step 4. To an acetonitrile solution (0.06 M) of 3-(3-(4-bromophenyl)propyl)-4,4-dimethyl-1H-pyrazol-5(4H)-one (1 eq.) from the previous step was added 4-tert-butylbenzyl bromide (1.1 eq.) and cesium carbonate (3 eq.). The resulting mixture was then heated at 50° C. for 16 h. After cooling the reaction suspension to RT, the volatiles were removed in vacuo and the resulting residue was partitioned between DCM and 10% aq. HCl. The organic layer was then washed further with water and brine, dried over Na$_2$SO$_4$, filtered and the filtrate concentrated in vacuo. Purification of the crude product thus obtained by way of column chromatography (SiO$_2$, gradient elution, Hex→3:2 (v/v) Hex: EtOAc) afforded the desired product as a colorless oil (91% yield).

Step 5: To a 3:1 (v/v) dioxane: water solution (0.1 M) of 3-(3-(4-bromophenyl)propyl)-1-(4-(tert-butyl)benzyl)-4,4-dimethyl-1H-pyrazol-5(4H)-one (1 eq.) from the previous step was added methyl 2-(2-methoxy-5-(4,4,5,5-tetramethyl-1,3,2-dioxaborolan-2-yl)phenyl)acetate (1.1 eq., prepared according to the patent procedure found in WO/2013/134562), tetrakis(triphenylphosphine)palladium(0) (0.1 eq.) and sodium bicarbonate (15 eq.). The resulting biphasic mixture was deoxygenated via sub-surface purging with a stream of nitrogen for 15 min. The reaction vessel was then tightly sealed and the reaction mixture was heated at 85° C. for 16 h. After cooling the reaction suspension to RT, the reaction was carefully quenched with 10% aq. HCl and extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, isocratic elution, 7:3 (v/v) Hex: EtOAc) afforded the desired product as a pale yellow oil (60% yield).

Step 6: To a 2:1 (v/v) THF: MeOH solution (0.035 M) of methyl 2-(4'-(3-(1-(4-(tert-butyl)benzyl)-4,4-dimethyl-5-oxo-4,5-dihydro-1H-pyrazol-3-yl)propyl)-4-ethoxy-[1,1'-biphenyl]-3-yl)acetic acid (1 eq.) from the previous step was added lithium hydroxide (10 eq., 2 N aq. solution). The resulting biphasic mixture was then stirred at RT for 48 h. The volatiles were then removed in vacuo and the resulting residue was acidified with 20% aq. citric acid. The aqueous suspension thus obtained was then extracted with EtOAc. The combined organic extracts were then washed further with water and brine, dried over Na$_2$SO$_4$, and filtered. Concentration of the filtrate in vacuo afforded the title compound as a white foam (99% yield). LC-MS: 555 (M+H)$^+$.

Example 56: 2-(4'-(3-(4,4-dimethyl-5-oxo-1-(4-(trifluoromethyl)phenyl)-4,5-dihydro-1H-pyrazol-3-yl)propyl)-4-ethoxy-[1,1'-biphenyl]-3-yl)acetic acid

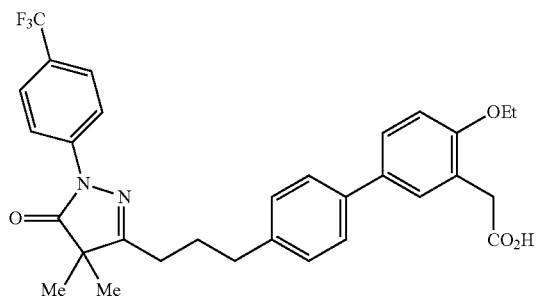 [SMILES: CCOc1ccc(-c2ccc(CCCC3=NN(c4ccc(C(F)(F)F)cc4)C(=O)C3(C)C)cc2)cc1CC(=O)O]

Prepared in an analogous manner to Example 55 but the functionalization of the pyrazalone core (i.e. step 4) is carried out as follows: To a DMSO solution (0.21 M) of 3-(3-(4-bromophenyl)propyl)-4,4-dimethyl-1H-pyrazol-5(4H)-one (1 eq.) from the previous step was added 4-iodobenzotrifluoride (1.5 eq.), copper(I) iodide (0.1 eq.), L-proline (0.2 eq.) and potassium carbonate (3 eq.). The resulting suspension was then deoxygenated via sub-surface purging with a stream of nitrogen for 15 min. Then, the reaction vessel was tightly sealed and the reaction mixture was heated at 95° C. for 16 h. After cooling the reaction suspension to RT, the reaction was carefully quenched with 10% aq. HCl and extracted with ether. The combined organic extracts were then washed further with water and brine, dried over Na$_2$SO$_4$, filtered and the filtrate concentrated in vacuo. Purification of the crude product thus obtained by way of column chromatography (SiO$_2$, gradient elution, 9:1→3:7 (v/v) Hex: EtOAc) afforded the desired product as a pinkish solid. LC-MS: 553 (M+H)$^+$.

Example 57: 3-(3-(4'-(3-fluorooxetan-3-yl)-[1,1'biphenyl]-4-yl)propyl)-4,4-dimethyl-1-(4-(trifluoromethyl)phenyl)-1H-pyrazol-5(4H)-one

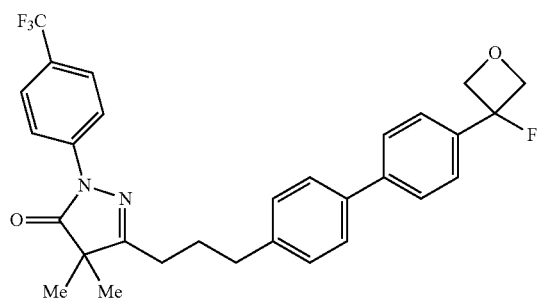 [SMILES: CC1(C)C(=O)N(c2ccc(C(F)(F)F)cc2)N=C1CCCc1ccc(-c2ccc(C3(F)COC3)cc2)cc1]

To a 2:1 (v/v) DME: water solution (0.11 M) of 3-(3-(4-bromophenyl)propyl)-4,4-dimethyl-1-(4-(trifluoromethyl)phenyl)-1H-pyrazol-5(4H)-one (1 eq., Example 56, Step 4) was added 2-(4-(3-fluorooxetan-3-yl)phenyl)-4,4,5,5-tetramethyl-1,3,2-dioxaborolane (1.2 eq., prepared according to the patent procedure found in WO/2013/134562), tetrakis(triphenylphosphine)palladium(0) (0.1 eq.) and potassium carbonate (3 eq.). The resulting biphasic mixture was deoxygenated via sub-surface purging with a stream of nitrogen for 15 min. The reaction vessel was then tightly sealed and the reaction mixture was heated at 90° C. for 16 h. After cooling the reaction suspension to RT, the reaction was carefully quenched with 10% aq. HCl and extracted with ether. The combined organic extracts were then washed further with 1 N aq. NaOH, water and brine, dried over Na$_2$SO$_4$, filtered and the filtrate concentrated in vacuo. Purification of the crude product thus obtained by way of column chromatography (SiO$_2$, isocratic elution, 7:3 (v/v) Hex: EtOAc) afforded the title product as a white solid (55% yield). LC-MS: 525 (M+H)$^+$.

Example 58: N-(6-(4-(3-(1-(4-(tert-butyl)benzyl)-4,4-dimethyl-5-oxo-4,5-dihydro-1H-pyrazol-3-yl)propyl)phenyl)pyridin-3-yl)benzenesulfonamide

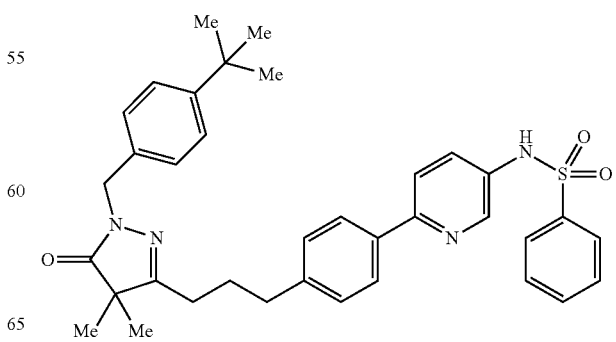

Step 1: To a dioxane solution (0.08 M) of 3-(3-(4-bromophenyl)propyl)-1-(4-(tert-butyl)benzyl)-4,4-dimethyl-1H-pyrazol-5(4H)-one (1 eq., Example 55, Step 4) was added potassium acetate (3 eq.), bis(pinacolato)diboron (1.3 eq.) and Pd(dppf)Cl$_2$ (0.1 eq.). The resulting pink suspension was deoxygenated via sub-surface purging with a stream of nitrogen for 15 min. The reaction vessel was then tightly sealed and the reaction mixture was heated at 85° C. for 16 h. The volatiles were then removed in vacuo and the resulting residue was partitioned between EtOAc and water. The organic extract was washed further with brine, dried over Na$_2$SO$_4$, filtered and the filtrate concentrated in vacuo. Purification of the crude product thus obtained by way of column chromatography (SiO$_2$, gradient elution, Hex→3:2 (v/v) Hex: EtOAc) afforded the desired product as a pale yellow oil (73% yield)

Step 2: To a 3:1 (v/v) dioxane: water solution (0.035 M) of 1-(4-(tert-butyl)benzyl)-4,4-dimethyl-3-(3-(4-(4,4,5,5-tetramethyl-1,3,2-dioxaborolan-2-yl)phenyl)propyl)-1H-pyrazol-5(4H)-one (1 eq.) from the previous step was added N-(6-bromopyridin-3-yl)benzenesulfonamide (1.1 eq.), tetrakis(triphenylphosphine)palladium(0) (0.1 eq.) and sodium bicarbonate (15 eq.). The resulting biphasic mixture was deoxygenated via sub-surface purging with a stream of nitrogen for 5 min. The reaction vessel was then tightly sealed and the reaction mixture was heated at 90° C. for 16 h. After cooling to RT, the reaction mixture was diluted with EtOAc and washed with water and brine. The organic extract was then dried over Na$_2$SO$_4$, filtered and the filtrate concentrated in vacuo. Purification of the crude product thus obtained by way of column chromatography (SiO$_2$, isocratic elution, 45:55 (v/v) Hex: EtOAc) afforded the title product as an off-white solid (45% yield). LC-MS: 609 (M+H)$^+$.

Example 59: N-(6-(4-(3-(1-(4-(tert-butyl)benzyl)-4,4-dimethyl-5-oxo-4,5-dihydro-1H-pyrazol-3-yl)propyl)phenyl)-3-methoxypyridin-2-yl)benzenesulfonamide

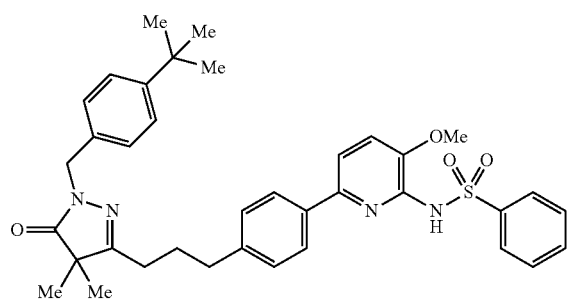 [SMILES: COc1ccc(-c2ccc(CCCC3=NN(Cc4ccc(C(C)(C)C)cc4)C(=O)C3(C)C)cc2)nc1NS(=O)(=O)c1ccccc1]

Step 1: To a 3:1 (v/v) dioxane: water solution (0.036 M) of 1-(4-(tert-butyl)benzyl)-4,4-dimethyl-3-(3-(4-(4,4,5,5-tetramethyl-1,3,2-dioxaborolan-2-yl)phenyl)propyl)-1H-pyrazol-5(4H)-one (1 eq., Example 58, step 1) was added 6-bromo-3-methoxy-2-nitropyridine (1.1 eq.), tetrakis(triphenylphosphine)palladium(0) (0.1 eq.) and sodium bicarbonate (15 eq.). The resulting biphasic mixture was deoxygenated via sub-surface purging with a stream of nitrogen for 5 min. The reaction vessel was then tightly sealed and the reaction mixture was heated at 90° C. for 16 h. After cooling to RT, the reaction mixture was diluted with EtOAc and washed with water and brine. The organic extract was then dried over Na$_2$SO$_4$, filtered and the filtrate concentrated in vacuo. Purification of the crude product thus obtained by way of column chromatography (SiO$_2$, isocratic elution, 45:55 (v/v) Hex: EtOAc) afforded the desired product as an off-white solid (80% yield).

Step 2: To a 1:1 (v/v) methanol: EtOAc solution (0.02 M) of 1-(4-(tert-butyl)benzyl)-3-(3-(4-(5-methoxy-6-nitropyridin-2-yl)phenyl)propyl)-4,4-dimethyl-1H-pyrazol-5(4H)-one (1 eq.) from the previous step was added was added palladium black (0.1 eq., 10% w/w (dry) over carbon). The resulting suspension was evacuated and back-filled with hydrogen gas (3×). Then, the reaction mixture was stirred under a static hydrogen atmosphere maintained with a balloon for 16 h. The mixture was carefully quenched with DCM and filtered through a bed of DCM-wetted celite. The insolubles were then washed further with DCM. Concentration of the filtrate thus obtained in vacuo furnished the desired product as an off-white solid (88% yield).

Step 3: To a pyridine solution (0.04 M) of 3-(3-(4-(6-amino-5-methoxypyridin-2-yl)phenyl)propyl)-1-(4-(tert-butyl)benzyl)-4,4-dimethyl-1H-pyrazol-5(4H)-one (1 eq.) from the previous step was added benzenesulfonyl chloride (1.1 eq.). After 16 h of stirring at RT, the volatiles were then removed in vacuo and the resulting residue was taken up in EtOAc. The EtOAc extract was then washed sequentially with sat. aq. CuSO$_4$, sat. aq. NaHCO$_3$, water and brine, dried over Na$_2$SO$_4$, filtered and the filtrate concentrated in vacuo. Purification of the crude product thus obtained by way of column chromatography (SiO$_2$, isocratic elution, 3:2 (v/v) Hex: Acetone) afforded the desired product as a beige solid (16% yield). LC-MS: 639 (M+H)$^+$.

What is claimed is:

1. A compound of Formula I

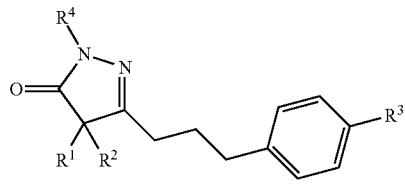

or a pharmaceutically acceptable salt thereof wherein:
$R^1$ and $R^2$ are each independently —C$_{1-6}$alkyl, optionally mono-, di- or tri-substituted with halogen, or
$R^1$ and $R^2$ are joined together to form —C$_{3-6}$cycloalkyl, optionally mono- or di-substituted with substituents independently selected from halogen, —C$_{1-6}$alkyl and —CF$_3$;
$R^3$ is selected from the group consisting of:
(a)

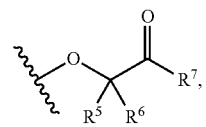

(b) aryl,
(c) heteroaryl,
(d)

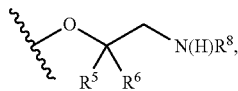

(e)

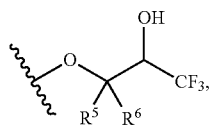

wherein the aryl of choice (b) and the heteroaryl of choice (c) are optionally mono- or di-substituted with substituents independently selected from —N(H)R$^8$, —C$_{1-6}$alkyl, —C$_{1-6}$alkyl-C(=O)OH, C$_{1-6}$alkoxy, halo-C$_{1-6}$alkyl, halo-C$_{1-6}$alkoxy, and

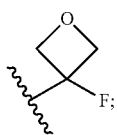 [SMILES: *C1(F)COC1]

R$^4$ is selected from the group consisting of:
  (a) aryl,
  (b) heteroaryl,
  (c) —C$_{1-2}$alkyl-aryl, and
  (d) —C$_{1-2}$alkyl-heteroaryl,
wherein the aryl of choices (a) and (c), and the heteroaryl of choices (b) and (d), are optionally mono- or di-substituted with substituents selected from the group consisting of halogen, —C$_{1-6}$alkyl, —CF$_3$, —OCF$_3$ C$_{1-6}$alkoxy, —C$_{3-6}$cycloalkoxy, halo-C$_{1-6}$alkyl, aryl, heteroaryl, heterocyclyl, —C$_{3-6}$cycloalkyl, and —C$_{3-6}$cycloalkenyl;
R$^5$ and R$^6$ are each independently selected from the group consisting of:
  (a) hydrogen,
  (b) —C$_{1-6}$alkyl,
  (c) aryl, and
  (d) hetereoaryl,
wherein the aryl of choice (c) and heteroaryl of choice (d) are optionally mono- or di-substituted with substituents independently selected from halogen, —C$_{1-6}$alkyl and —CF$_3$ or
R$^5$ and R$^6$ are joined together to form a —C$_{3-6}$cycloalkyl optionally mono- or di-substituted with substituents independently selected from halogen, —C$_{1-6}$alkyl and —CF$_3$;
R$^7$ is selected from the group consisting of:
  (a) hydroxyl,
  (b) —N(H)S(=O)$_2$aryl,
  (c) —N(H)S(=O)$_2$heteroaryl,
  (d) —N(H)S(=O)$_2$—C$_{3-6}$cycloalkyl,
  (e) —N(H)S(=O)$_2$—C$_{1-6}$alkyl,
  (f) —N(H)-aryl,
  (g) —N(H)-heteroaryl,
  (h) —N(H)—C$_{3-6}$cycloalkyl,
  (i) —N(H)—C$_{1-6}$alkyl, and
  (j) —CF$_3$,
wherein the aryl of choices (b) and (f), the heteroaryl of choices (c) and (g), the alkyl portion of choices (e) and (i), and the cycloalkyl portion of choices (d) and (h), are optionally mono- or di-substituted with substituents independently selected from halogen, —C$_{1-6}$alkyl, —CF$_3$, —C$_{3-6}$cycloalkyl, C$_{1-6}$alkoxy, C$_{3-6}$cycloalkoxy, aryl, heteroaryl, and hydroxyl; and R$^8$ is selected from the group consisting of:
  (a) hydrogen,
  (b) —S(=O)$_2$aryl,
  (c) —S(=O)$_2$heteroaryl,
  (d) —C(=O)aryl,
  (e) —C(=O)heteroaryl,
  (f) —S(=O)$_2$—C$_{1-6}$alkyl,
  (g) —S(=O)$_2$—C$_{3-6}$cycloalkyl,
  (h) —C(=O)—C$_{1-6}$alkyl, and
  (i) —C(=O)—C$_{3-6}$cycloalkyl,
wherein the aryl of choices (b) and (d), and the heteroaryl of choices (c) and (e), the alkyl portion of choices (f) and (h), and the cycloalkyl portion of choices (g) and (i), are optionally mono- or di-substituted with substituents independently selected from halogen, —C$_{1-6}$alkyl, —CF$_3$, —C$_{3-6}$cycloalkyl, C$_{1-6}$alkoxy, C$_{3-6}$cycloalkoxy, aryl, heteroaryl, and hydroxyl.

2. A compound according to claim 1 or a pharmaceutically acceptable salt thereof wherein: R$^1$ and R$^2$ are each independently methyl, optionally mono-, di- or tri-substituted with halogen or R$^1$ and R$^2$ are joined together to form —C$_{3-6}$cycloalkyl, optionally mono or di-substituted with substituents independently selected from halogen, —C$_{1-6}$alkyl and —CF$_3$.

3. A compound according to claim 2 or a pharmaceutically acceptable salt thereof wherein: R$^1$ and R$^2$ are each independently methyl, optionally mono-, di- or tri-substituted with halogen.

4. A compound according to claim 1 of formula Ia:

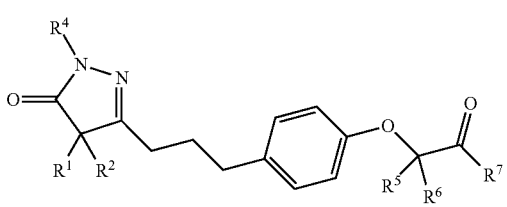

or a pharmaceutically acceptable salt thereof.

5. A compound according to claim 1 or a pharmaceutically acceptable salt thereof wherein: R$^4$ is elected from the group consisting of:
  (a) -phenyl,
  (b) -pyridyl,
  (c) —CH$_2$-phenyl, and
  (d) —CH$_2$-pyridyl,
wherein the phenyl portion of choices (a) and (c), and the pyridyl portion of choices (b) and (d), are optionally mono- or di-substituted with substituents selected from the group consisting of halogen, —C$_{1-6}$alkyl, —CF$_3$, —OCF$_3$, —C$_{1-6}$alkoxy, —C$_{3-6}$cycloalkyl, C$_{3-6}$cycloalkoxy, and halo-C$_{1-6}$alkyl.

6. A compound according to claim 1 or a pharmaceutically acceptable salt thereof wherein: R$^5$ and R$^6$ are joined together to form a —C$_{3-6}$cycloalkyl.

7. A compound according to claim 1 or a pharmaceutically acceptable salt thereof wherein: R$^7$ is selected from the group consisting of:
  (a) hydroxyl,
  (b) —N(H)S(=O)$_2$aryl,
  (c) —N(H)S(=O)$_2$heteroaryl,
  (d) —N(H)S(=O)$_2$—C$_{3-6}$cycloalkyl, and
  (e) —N(H)S(=O)$_2$—C$_{1-6}$alkyl, wherein the aryl portion of choice (b), the heteroaryl portion of choice (c), the cycloalkyl portion of choice (d) and the alkyl portion of choice (e) are optionally mono- or di-substituted with substituents independently selected from halogen, —$C_{1-6}$alkyl, —$CF_3$, —$C_{3-6}$cycloalkyl, $C_{1-6}$alkoxy, $C_{3-6}$cycloalkoxy, aryl, heteroaryl, and hydroxyl.

8. A compound according to claim 7 or a pharmaceutically acceptable salt thereof wherein: $R^7$ is hydroxyl.

9. A compound according to claim 1 or a pharmaceutically acceptable salt thereof wherein: $R^8$ is selected from the group consisting of:
   (a) hydrogen,
   (b) —S(=O)$_2$aryl,
   (c) —S(=O)$_2$heteroaryl,
   (d) —C(=O)aryl, and
   (e) —C(=O)heteroaryl,
wherein the aryl of choices (b) and (d), and the heteroaryl of choices (c) and (e), are optionally mono- or di-substituted with substituents independently selected from halogen, —$C_{1-6}$alkyl, —$CF_3$, —$C_{3-6}$cycloalkyl, $C_{1-6}$alkoxy, $C_{3-6}$cycloalkoxy, aryl, heteroaryl, and hydroxyl.

10. A compound according to claim 1 of formula Ia:

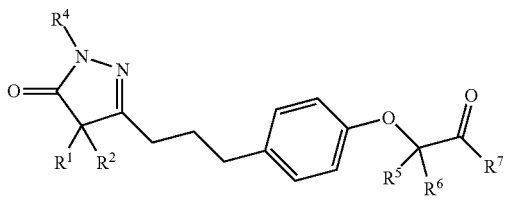

Ia or a pharmaceutically acceptable salt thereof wherein:
$R^1$ and $R^2$ are each independently methyl, optionally mono-, di- or tri-substituted with halogen, or
$R^1$ and $R^2$ are joined together to form —$C_{3-6}$cycloalkyl, optionally mono or di-substituted with substituents independently selected from halogen, —$C_{1-6}$alkyl and —$CF_3$;
$R^4$ is selected from the group consisting of:
   (a) -phenyl,
   (b) -pyridyl,
   (c) —$CH_2$-phenyl, and
   (d) —$CH_2$-pyridyl,
wherein the phenyl portion of choices (a) and (c), and the pyridyl portion of choices (b) and (d), are optionally mono- or di-substituted with substituents selected from the group consisting of halogen, —$C_{1-6}$alkyl, —$CF_3$, —$OCF_3$, $C_{1-6}$alkoxy, —$C_{3-6}$cycloalkyl, $C_{3-6}$cycloalkoxy, and halo-$C_{1-6}$alkyl;
$R^5$ and $R^6$ are joined together to form a —$C_{3-6}$cycloalkyl; and
$R^7$ is selected from the group consisting of:
   (a) hydroxyl,
   (b) —N(H)S(=O)$_2$aryl,
   (c) —N(H)S(=O)$_2$heteroaryl,
   (d) —N(H)S(=O)$_2$—$C_{3-6}$cycloalkyl, and
   (e) —N(H)S(=O)$_2$—$C_{1-6}$alkyl,
wherein the aryl portion of choice (b), the heteroaryl portion of choice (c), the cycloalkyl portion of choice (d) and the alkyl portion of choice (e) are optionally mono- or di-substituted with substituents independently selected from halogen, —$C_{1-6}$alkyl, —$CF_3$, —$C_{3-6}$cycloalkyl, —$C_{1-6}$alkoxy, $C_{3-6}$cycloalkoxy, aryl, heteroaryl, and hydroxyl.

11. A compound according to claim 10 or a pharmaceutically acceptable salt thereof wherein: $R^7$ is hydroxyl.

12. A compound according to claim 1 selected from the group consisting of
2-(4-(3-(1-(4-(tert-butyl)benzyl)-4,4-dimethyl-5-oxo-4,5-dihydro-1H-pyrazol-3-yl)propyl)phenoxy)-2-methylpropanoic acid,
2-(4-(3-(1-(4-(tert-butyl)benzyl)-4,4-dimethyl-5-oxo-4,5-dihydro-1H-pyrazol-3-yl)propyl)phenoxy)-2-methyl-N-(phenylsulfonyl)propanamide,
N-benzyl-2-(4-(3-(1-(4-(tert-butyl)benzyl)-4,4-dimethyl-5-oxo-4,5-dihydro-1H-pyrazol-3-yl)propyl)phenoxy)-2-methylpropanamide,
2-(4-(3-(1-(4-(tert-butyl)benzyl)-4,4-dimethyl-5-oxo-4,5-dihydro-1H-pyrazol-3-yl)propyl)phenoxy)-2-methyl-N-(pyridin-2-ylmethyl)propanamide,
2-(4-(3-(1-(4-(tert-butyl)benzyl)-4,4-dimethyl-5-oxo-4,5-dihydro-1H-pyrazol-3-yl)propyl)phenoxy)-2-methyl-N-(pyridin-4-ylmethyl)propanamide,
2-(4-(3-(1-(4-(tert-butyl)benzyl)-4,4-dimethyl-5-oxo-4,5-dihydro-1H-pyrazol-3-yl)propyl)phenoxy)-N-(cyclohexylmethyl)-2-methylpropanamide,
2-(4-(3-(4,4-dimethyl-5-oxo-1-(3-(trifluoromethyl)benzyl)-4,5-dihydro-1H-pyrazol-3-yl)propyl)phenoxy)-2-methylpropanoic acid,
2-(4-(3-(4,4-dimethyl-5-oxo-1-(4-(trifluoromethyl)benzyl)-4,5-dihydro-1H-pyrazol-3-yl)propyl)phenoxy)-2-methylpropanoic acid,
2-(4-(3-(4,4-dimethyl-5-oxo-1-phenethyl-4,5-dihydro-1H-pyrazol-3-yl)propyl)phenoxy)-2-methylpropanoic acid,
2-(4-(3-(4,4-dimethyl-5-oxo-1-phenyl-4,5-dihydro-1H-pyrazol-3-yl)propyl)phenoxy)-2-methylpropanoic acid,
2-(4-(3-(1-(4-(tert-butyl)phenyl)-4,4-dimethyl-5-oxo-4,5-dihydro-1H-pyrazol-3-yl)propyl)phenoxy)-2-methylpropanoic acid,
2-(4-(3-(1-(4-isopropylbenzyl)-4,4-dimethyl-5-oxo-4,5-dihydro-1H-pyrazol-3-yl)propyl)phenoxy)-2-methylpropanoic acid,
2-(4-(3-(1-(4-bromobenzyl)-4,4-dimethyl-5-oxo-4,5-dihydro-1H-pyrazol-3-yl)propyl)phenoxy)-2-methylpropanoic acid,
2-(4-(3-(1-([1,1'-biphenyl]-4-ylmethyl)-4,4-dimethyl-5-oxo-4,5-dihydro-1H-pyrazol-3-yl)propyl)phenoxy)-2-methylpropanoic acid,
2-(4-(3-(4,4-dimethyl-5-oxo-1-((2',3',4',5'-tetrahydro-[1,1'-biphenyl]-4-yl)methyl)-4,5-dihydro-1H-pyrazol-3-yl)propyl)phenoxy)-2-methylpropanoic acid,
2-(4-(3-(1-(4-cyclopropylbenzyl)-4,4-dimethyl-5-oxo-4,5-dihydro-1H-pyrazol-3-yl)propyl)phenoxy)-2-methylpropanoic acid,
2-(4-(3-(1-(4-cyclohexylbenzyl)-4,4-dimethyl-5-oxo-4,5-dihydro-1H-pyrazol-3-yl)propyl)phenoxy)-2-methylpropanoic acid,
2-(4-(3-(1-(3-fluoro-4-(trifluoromethyl)benzyl)-4,4-dimethyl-5-oxo-4,5-dihydro-1H-pyrazol-3-yl)propyl)phenoxy)-2-methylpropanoic acid,
2-(4-(3-(4,4-dimethyl-5-oxo-1-(4-(trifluoromethyl)phenyl)-4,5-dihydro-1H-pyrazol-3-yl)propyl)phenoxy)-2-methylpropanoic acid,
2-(4-(3-(4,4-dimethyl-5-oxo-1-(3-(trifluoromethyl)phenyl)-4,5-dihydro-1H-pyrazol-3-yl)propyl)phenoxy)-2-methylpropanoic acid,
2-(4-(3-(4,4-dimethyl-5-oxo-1-(5-(trifluoromethyl)pyridin-2-yl)-4,5-dihydro-1H-pyrazol-3-yl)propyl)phenoxy)-2-methylpropanoic acid, 2-(4-(3-(4,4-dimethyl-5-oxo-1-(4-(trifluoromethyl)phenyl)-4,5-dihydro-1H-pyrazol-3-yl)propyl)phenoxy)-2-methyl-N-(phenyl sulfonyl)propanamide, 2-(4-(3-(3-(4-(tert-butyl)benzyl)-4-oxo-2,3-diazaspiro[4,4]non-1-en-1-yl)propyl)phenoxy)-2-methylpropanoic acid, 2-methyl-2-(4-(3-(4-oxo-3-(4-(trifluoromethyl)phenyl)-2,3-diazaspiro[4,4]non-1-en-1-yl)propyl)phenoxy)propanoic acid, 2-methyl-2-(4-(3-(4-oxo-3-(4-(trifluoromethyl)phenyl)-2,3-diazaspiro[4,4]non-1-en-1-yl)propyl)phenoxy)-N-(phenylsulfonyl)propanamide, N-cyclopropyl-2-methyl-2-(4-(3-(4-oxo-3-(4-(trifluoromethyl)phenyl)-2,3-diazaspiro[4,4]non-1-en-1-yl)propyl)phenoxy)propanamide, 2-methyl-2-(4-(3-(4-oxo-3-(4-(trifluoromethyl)phenyl)-2,3-diazaspiro[4,4]non-1-en-1-yl)propyl)phenoxy)-N-(2,2,2-trifluoroethyl)propanamide, 2-methyl-2-(4-(3-(4-oxo-3-(4-(trifluoromethoxy)phenyl)-2,3-diazaspiro[4,4]non-1-en-1-yl)propyl)phenoxy)propanoic acid, N-cyclopropyl-2-methyl-2-(4-(3-(4-oxo-3-(4-(trifluoromethoxy)phenyl)-2, 3-diazaspiro[4,4]non-1-en-1-yl)propyl)phenoxy)propanamide, 2-methyl-2-(4-(3-(4-oxo-3-(4-(trifluoromethoxy)phenyl)-2,3-diazaspiro[4,4]non-1-en-1-yl)propyl)phenoxy)-N-(2,2,2-trifluoroethyl)propanamide, 2-(4-(3-(3-(3,4-dimethylphenyl)-4-oxo-2,3-diazaspiro[4,4]non-1-en-1-yl)propyl)phenoxy)-2-methylpropanoic acid, N-cyclopropyl-2-(4-(3-(3-(3,4-dimethylphenyl)-4-oxo-2,3-diazaspiro[4,4]non-1-en-1-yl)propyl)phenoxy)-2-methylpropanamide, 2-(4-(3-(3-(3,4-dimethylphenyl)-4-oxo-2,3-diazaspiro[4,4]non-1-en-1-yl)propyl)phenoxy)-2-methyl-N-(2,2,2-trifluoroethyl)propanamide, 2-methyl-2-(4-(3-(4-oxo-3-(4-(trifluoromethyl)benzyl)-2,3-diazaspiro[4,4]non-1-en-1-yl)propyl)phenoxy)propanoic acid, 2-methyl-2-(4-(3-(4-oxo-3-(3-(trifluoromethyl)phenyl)-2,3-diazaspiro[4,4]non-1-en-1-yl)propyl)phenoxy)propanoic acid, 2-methyl-2-(4-(3-(4-oxo-3-(3-(trifluoromethoxy)phenyl)-2,3-diazaspiro[4,4]non-1-en-1-yl)propyl)phenoxy)propanoic acid, 2-methyl-2-(4-(3-(3-(naphthalen-2-yl)-4-oxo-2,3-diazaspiro[4,4]non-1-en-1-yl)propyl)phenoxy)propanoic acid, 2-(4-(3-(3-([1,1'-biphenyl]-3-yl)-4-oxo-2,3-diazaspiro[4,4]non-1-en-1-yl)propyl)phenoxy)-2-methylpropanoic acid, 2-methyl-2-(4-(3-(3-(4-methyl-3-(trifluoromethyl)phenyl)-4-oxo-2,3-diazaspiro[4,4]non-1-en-1-yl)propyl)phenoxy)propanoic acid, 2-(4-(3-(3-(3-(tert-butyl)phenyl)-4-oxo-2,3-diazaspiro[4,4]non-1-en-1-yl)propyl)phenoxy)-2-methylpropanoic acid, 2-methyl-2-(4-(3-(5-oxo-4,4-dipropyl-1-(4-(trifluoromethyl)phenyl)-4,5-dihydro-1H-pyrazol-3-yl)propyl)phenoxy)propanoic acid, 2-methyl-2-(4-(3-(5-oxo-4,4-dipropyl-1-(3-(trifluoromethyl)phenyl)-4,5-dihydro-1H-pyrazol-3-yl)propyl)phenoxy)propanoic acid, 4,4-dimethyl-3-(3-(4-((4,4,4-trifluoro-3-hydroxy-2-methylbutan-2-yl)oxy)phenyl)propyl)-1-(4-(trifluoromethyl)phenyl)-1H-pyrazol-5(4H)-one, 4,4-dimethyl-3-(3-(4-((4,4,4-trifluoro-2-methyl-3-oxobutan-2-yl)oxy)phenyl)propyl)-1-(4-(trifluoromethyl)phenyl)-1H-pyrazol-5(4H)-one, 4-(3-(4-((1-amino-2-methylpropan-2-yl)oxy)phenyl)propyl)-2-(4-(trifluoromethyl)phenyl)-2,3-diazaspiro[4,4]non-3-en-1-one, N-(2-methyl-2-(4-(3-(4-oxo-3-(4-(trifluoromethyl)phenyl)-2,3-diazaspiro[4,4]non-1-en-1-yl)propyl)phenoxy)propyl)benzenesulfonamide, N-(2-methyl-2-(4-(3-(4-oxo-3-(4-(trifluoromethyl)phenyl)-2,3-diazaspiro[4,4]non-1-en-1-yl)propyl)phenoxy)propyl)benzamide, 2-(4-(3-(4,4-dimethyl-5-oxo-1-(4-(trifluoromethyl)phenyl)-4,5-dihydro-1H-pyrazol-3-yl)propyl)phenoxy)-2-phenylacetic acid, 2-(4-(3-(4,4-dimethyl-5-oxo-1-(4-(trifluoromethyl)phenyl)-4,5-dihydro-1H-pyrazol-3-yl)propyl)phenoxy)acetic acid, 1-(4-(3-(4,4-dimethyl-5-oxo-1-(4-(trifluoromethyl)phenyl)-4,5-dihydro-1H-pyrazol-3-yl)propyl)phenoxy)cyclobutanecarboxylic acid, 1-(4-(3-(4,4-dimethyl-5-oxo-1-(3-(trifluoromethyl)phenyl)-4,5-dihydro-1H-pyrazol-3-yl)propyl)phenoxy)cyclobutanecarboxylic acid, 1-(4-(3-(4,4-dimethyl-5-oxo-1-(4-(trifluoromethyl)phenyl)-4,5-dihydro-1H-pyrazol-3-yl)propyl)phenoxy)cyclopentanecarboxylic acid, 2-(4-(3-(4,4-dimethyl-5-oxo-1-(4-(trifluoromethyl)phenyl)-4,5-dihydro-1H-pyrazol-3-yl)propyl)phenoxy)-2-phenylpropanoic acid, 2-(4-(3-(4,4-dimethyl-5-oxo-1-(3-(trifluoromethyl)phenyl)-4,5-dihydro-1H-pyrazol-3-yl)propyl)phenoxy)-2-phenylpropanoic acid, 2-(4'-(3-(1-(4-(tert-butyl)benzyl)-4,4-dimethyl-5-oxo-4,5-dihydro-1H-pyrazol-3-yl)propyl)-4-ethoxy-[1,1'-biphenyl]-3-yl)acetic acid, 2-(4'-(3-(4,4-dimethyl-5-oxo-1-(4-(trifluoromethyl)phenyl)-4,5-dihydro-1H-pyrazol-3-yl)propyl)-4-ethoxy-[1,1'-biphenyl]-3-yl)acetic acid, 3-(3-(4'-(3-fluorooxetan-3-yl)-[1,1'biphenyl]-4-yl)propyl)-4,4-dimethyl-1-(4-(trifluoromethyl)phenyl)-1H-pyrazol-5(4H)-one, N-(6-(4-(3-(1-(4-(tert-butyl)benzyl)-4,4-dimethyl-5-oxo-4,5-dihydro-1H-pyrazol-3-yl)propyl)phenyl)pyridin-3-yl)benzenesulfonamide, and N-(6-(4-(3-(1-(4-(tert-butyl)benzyl)-4,4-dimethyl-5-oxo-4,5-dihydro-1H-pyrazol-3-yl)propyl)phenyl)-3-methoxypyridin-2-yl)benzenesulfonamide, or a pharmaceutically acceptable salt thereof.

13. A pharmaceutical composition comprising a compound according to claim 1, or a pharmaceutically acceptable salt thereof, and at least one pharmaceutically acceptable carrier.

14. A method of treating a cancer in a mammal, wherein the cancer is negatively impacted by diminution in its metabolism of fatty acid oxidation, comprising administration of a therapeutically effective amount of a compound of claim 1, or a pharmaceutically acceptable salt thereof, to the mammal in need thereof, wherein the cancer is selected from the group consisting of prostate, breast, ovarian, liver, kidney, colon, pancreatic, acute or chronic myeloid leukemia, human chronic lymphocytic leukemia, and melanoma.

15. A method of treating cancer in a mammal comprising the administration of a therapeutically effective amount of a compound according to claim 1, or a pharmaceutically acceptable salt thereof, to the mammal in need thereof, wherein the cancer is selected from the group consisting of prostate, breast, ovarian, liver, kidney, colon, pancreatic, acute or chronic myeloid leukemia, human chronic lymphocytic leukemia, and melanoma.

16. A method of treating a viral infection in a mammal comprising the administration of a therapeutically effective amount of a compound according to claim 1, or a pharmaceutically acceptable salt thereof to the mammal in need thereof, wherein the viral infection is a hepatitis C virus (HCV) infection or a human immunodeficiency virus (HIV) infection.

17. The method of claim 14, wherein the cancer is human chronic lymphocytic leukemia.

18. The method of claim 14 wherein the cancer is acute or chronic myeloid leukemia.

19. The compound of claim 1, selected from the group consisting of:

2-methyl-2-(4-(3-(4-oxo-3-(4-(trifluoromethyl)phenyl)-2,3-diazaspiro[4,4]non-1-en-1-yl)propyl) phenoxy) propanoic acid, 1-(4-(3-(4,4-dimethyl-5-oxo-1-(4-(trifluoromethyl)phenyl)-4,5-dihydro-1H-pyrazol-3-yl)propyl) phenoxy)cyclobutanecarboxylic acid, 1-(4-(3-(4,4-dimethyl-5-oxo-1-(4-(trifluoromethyl)phenyl)-4,5-dihydro-1H-pyrazol-3-yl)propyl) phenoxy)cyclopentanecarboxylic acid, 2-(4-(3-(4,4-dimethyl-5-oxo-1-(4-(trifluoromethyl)phenyl)-4,5-dihydro-1H-pyrazol-3-yl)propyl) phenoxy)-2-phenylpropanoic acid, and 2-(4-(3-(4,4-dimethyl-5-oxo-1-(3-(trifluoromethyl)phenyl)-4,5-dihydro-1H-pyrazol-3-yl)propyl) phenoxy)-2-phenylpropanoic acid, or a pharmaceutically acceptable salt thereof.

* * * * *